US008013853B1

(12) United States Patent
Douglas et al.

(10) Patent No.: US 8,013,853 B1
(45) Date of Patent: Sep. 6, 2011

(54) VIRTUAL DENTAL PATIENT

(75) Inventors: Bill Douglas, Falson Heights, MN (US);
Ralph DeLong, New Brighton, MN (US)

(73) Assignee: Regents of the University of Minnesota, St. Paul, MN (US)

(*) Notice: Subject to any disclaimer, the term of this patent is extended or adjusted under 35 U.S.C. 154(b) by 1506 days.

(21) Appl. No.: 10/385,169

(22) Filed: Mar. 6, 2003

Related U.S. Application Data

(60) Provisional application No. 60/362,410, filed on Mar. 6, 2002.

(51) Int. Cl.
*G06T 17/00* (2006.01)
(52) U.S. Cl. ...................................................... 345/420
(58) Field of Classification Search .................... 345/420
See application file for complete search history.

(56) References Cited

U.S. PATENT DOCUMENTS

| | | | |
|---|---|---|---|
| 4,234,306 A * | 11/1980 | Hamada et al. | 433/55 |
| 4,837,732 A | 6/1989 | Brandestini et al. | |
| 5,121,333 A | 6/1992 | Riley et al. | |
| 5,230,623 A | 7/1993 | Guthrie et al. | |
| 5,257,184 A | 10/1993 | Mushabac | |
| 5,338,198 A | 8/1994 | Wu et al. | |
| 5,340,309 A * | 8/1994 | Robertson | 433/69 |
| 5,343,391 A | 8/1994 | Mushabac | |
| 5,372,502 A | 12/1994 | Massen et al. | |
| 5,448,472 A | 9/1995 | Mushabac | |
| 5,545,039 A | 8/1996 | Mushabac | |
| 5,562,448 A | 10/1996 | Mushabac | |
| 5,569,578 A | 10/1996 | Mushabac | |
| 5,605,459 A | 2/1997 | Kuroda et al. | |
| 5,678,546 A | 10/1997 | Truppe | |
| 5,688,118 A | 11/1997 | Hayka et al. | |
| 5,704,897 A | 1/1998 | Truppe | |
| 5,798,924 A | 8/1998 | Eufinger et al. | |
| 5,823,958 A | 10/1998 | Truppe | |
| 5,842,858 A | 12/1998 | Truppe | |
| 5,846,081 A | 12/1998 | Bushway | |
| 5,882,192 A | 3/1999 | Bergersen | |

(Continued)

FOREIGN PATENT DOCUMENTS

| | | |
|---|---|---|
| EP | 025597 A1 | 2/1988 |
| EP | 0488987 B1 | 6/1992 |
| EP | 0652726 B1 | 5/1995 |
| EP | 0741994 A1 | 11/1996 |
| WO | WO-94/03100 A1 | 2/1994 |

OTHER PUBLICATIONS

"Overview—from Artma Biomedical website", http://www.artma.com/v2/Pages/about.htm, (observed Dec. 15, 1999), 7 pgs.

Millesi, W., et al., "Image-guided surgery extended by remote sterotactic visualization", *CVRMed-MRCAS '97. First Joint Conference, Computer Vision, Virtual Reality and Robotics in Medicine and Medical Robotics adn Computer-Assisted Surgery Proceedings*, (1997), 813-816.

Seipel, S., et al., "Oral Implant Treatment Planning in a Virtual Reality Environment", *Computer Methods and Programs in Biomedicine, 57*, (1998),95-103.

(Continued)

*Primary Examiner* — Xiao M Wu
*Assistant Examiner* — Edward Martello
(74) *Attorney, Agent, or Firm* — Schwegman, Lundberg & Woessner, P.A.

(57) ABSTRACT

Systems and methods read clinical data records to create and three-dimensional images representing a virtual dental patient. The images can be used to assess the current dental health of a patient. In particular the systems and methods create accurate, three-dimensional virtual renditions of dental patients, compare the virtual renditions with other virtual renditions, and create computer databases of the renditions from which population statistics are calculated for parameters measured on the renditions. By comparing a particular patient rendition to the population statistics a report is produced that aids in the diagnosis of the patient's current dental health.

25 Claims, 29 Drawing Sheets

U.S. PATENT DOCUMENTS

| | | | |
|---|---|---|---|
| 5,905,658 A * | 5/1999 | Baba | 703/7 |
| 5,967,777 A | 10/1999 | Klein et al. | |
| 5,986,662 A | 11/1999 | Argiro et al. | |
| 6,152,731 A * | 11/2000 | Jordan et al. | 433/69 |
| 6,315,553 B1 * | 11/2001 | Sachdeva et al. | 433/24 |
| 6,318,994 B1 * | 11/2001 | Chishti et al. | 433/24 |
| 6,464,496 B1 * | 10/2002 | Sachdeva et al. | 433/24 |
| 6,471,512 B1 * | 10/2002 | Sachdeva et al. | 433/24 |
| 6,540,512 B1 * | 4/2003 | Sachdeva et al. | 433/24 |
| 6,621,491 B1 * | 9/2003 | Baumrind et al. | 345/419 |
| 6,688,885 B1 * | 2/2004 | Sachdeva et al. | 433/24 |
| 7,027,642 B2 * | 4/2006 | Rubbert et al. | 382/154 |
| 2002/0010568 A1 * | 1/2002 | Rubbert et al. | 703/6 |
| 2002/0042038 A1 * | 4/2002 | Miller et al. | 433/24 |
| 2002/0180760 A1 * | 12/2002 | Rubbert et al. | 345/630 |
| 2003/0105611 A1 * | 6/2003 | Sachdeva | 702/153 |

OTHER PUBLICATIONS

Shimabukuro, M. H., et al., "Visualisation and Reconstruction in Dentisrty", *Proceedings of the IEEE Conference on Information Visualization*, (1998),25-31.

Snow, M. D., et al., "Chapter 48—Interactive Computer Technologies in Dentistry. Virtual Reality in Orthondontics", *Medicine Meets Virtual Reality. Health Care in the Information Age. Proceedings of Medicine Meets Virtual Reality 4*, (1996), 411-422.

Truppe, M. J., et al., "Interventional Video Tomography", *SPIE Proceedings of Lasers in Surgery*, (1995), 150-152.

Vannier, M. W., et al., "3D Dental Imaging by Spiral CT", http://www.erl.wustl.edu/Proj_web/Dental/3dd_sCT.html, (observed Dec. 10, 1999), 13 pgs.

* cited by examiner 330   331

VIRTUAL DENTAL PATIENT

CROSS-REFERENCE TO RELATED APPLICATIONS

The application claims priority to U.S. provisional patent application Ser. No. 60/362,410, entitled "Virtual Dental Patient," filed Mar. 6, 2002, which is hereby incorporated by reference.

STATEMENT OF GOVERNMENT RIGHTS

This invention was made with Government support under grant# R01-DE12225 awarded by NIH/NIDCR. The Government has certain rights in this invention.

FIELD

The present invention relates generally to computerized systems for rendering medical data, and more particularly to rendering images of a virtual dental patient based on scanned and computed data.

COPYRIGHT NOTICE/PERMISSION

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the software and data as described below and in the drawings hereto: Copyright© 2002, University of Minnesota. All Rights Reserved.

BACKGROUND

As computer systems and scanning systems have become capable of acquiring and displaying results with ever-increasing resolution, it has become possible to render images of scanned data with increasing accuracy and realism. In addition, scanning and rendering three-dimensional data is now commonplace. One application of these systems has been in the area of medical imaging, and more particularly, in the area of dental imaging. In these systems, scanned data is used to render three-dimensional images obtained by scanners such as CT (Computer Tomography), MRI (Magnetic Resonance Imaging) and other forms of scanned data. Typically, the scanned data is transformed into a network of polygons that represent the surfaces that were scanned. These polygons are then rendered using three-dimensional computer graphics software and hardware.

While such systems have been successful in capturing and rendering dental related data, several problems remain with these systems. First, there has to date been no way to accurately and independently represent the motion of the lower jaw in relation to the upper jaw using clinical records. The motion of the lower jaw in relation to the upper jaw is complex. For example, the lower jaw is capable of opening, closing, and moving in both a lateral (i.e. side to side) and protrusive (i.e. front to back) manner. To date, no system has been capable of accurately modeling this complex motion.

As a result, there is a need in the art for a system that can provide accurate rendered images of a dental patient based on clinical records. In addition, there is a need in the art for such a system that can accurately model the movement of the jaw of a particular patient.

DETAILED DESCRIPTION

In the following detailed description of exemplary embodiments of the invention, reference is made to the accompanying drawings which form a part hereof, and in which is shown by way of illustration specific exemplary embodiments in which the invention may be practiced. These embodiments are described in sufficient detail to enable those skilled in the art to practice the invention, and it is to be understood that other embodiments may be utilized and that logical, mechanical, electrical and other changes may be made without departing from the scope of the present invention. The following detailed description is, therefore, not to be taken in a limiting sense.

In the Figures, the same reference number is used throughout to refer to an identical component that appears in multiple Figures. Signals and connections may be referred to by the same reference number or label, and the actual meaning will be clear from its use in the context of the description.

The detailed description is divided into multiple sections, and describes various aspects and embodiments of the invention, which will be collectively referred to as a Virtual Dental patient (VDP). In the first section, the software environment of varying embodiments of the invention is described. In the second section the hardware and operating environment of different embodiments of the invention is described. In the final section, a conclusion is provided.

Software Environment

Figure 1:
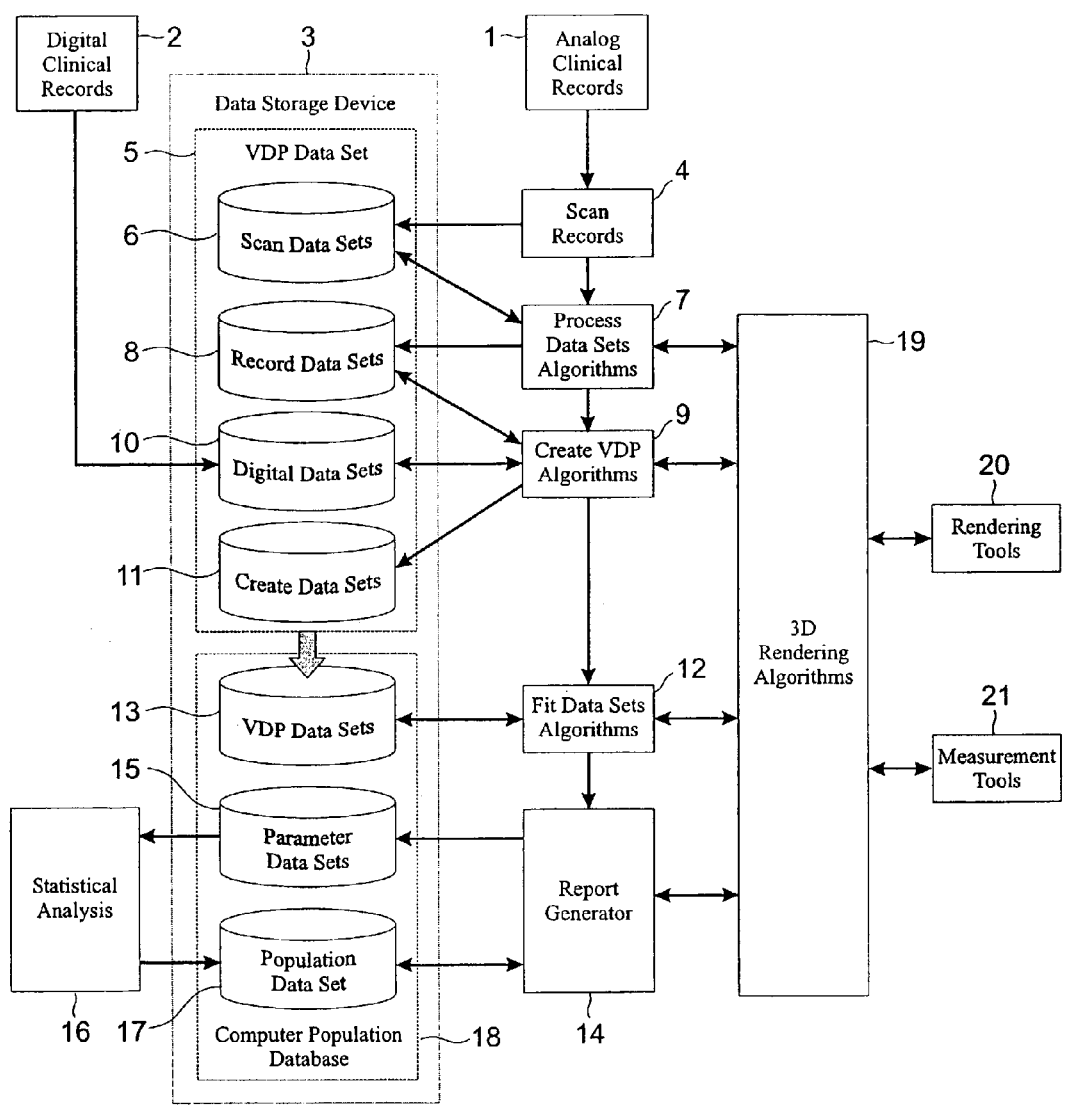
FIG. 1 is a block diagram illustrating the general order of workflow in accordance with an embodiment of the present invention.

The embodiments of the invention describe a software environment of systems and methods that create and maintain data representing a virtual dental patient. FIG. 1 is a block diagram illustrating the general order of workflow in accordance with an embodiment of the invention. The workflow describes rendering a graphical, or virtual rendition of a dental patient. It is desirable that the virtual renditions of the dental patient are accurate; therefore, clinical records of the patient are included in the input data used. Various types of records are possible, including analog records 1 and digital clinical records 2. Analog records are records that are scanned 4 and converted to a digital format. Examples of analog records 1 include impressions of the upper and lower jaws, which include any and all teeth plus the surrounding soft tissues, bite registration records, and functional registration records. Digital records 2 are records that are already in a useable digital format. Examples of digital records include jaw tracking data, 3D facial images, MRI and CT scans. Each digital clinical record forms a digital data set can be archived in the Digital Data Sets 10 that can reside in a Computer Storage Device 3. The Digital Data Sets 10 make up one part of the VDP data set 5. The clinical records will be described in more detail later in the description.

The data sets representing the analog clinical records contain the x, y, and z coordinates of points acquired by scanning the relevant surfaces of these records. The points can be acquired using any digitizing system that can produce a suitable point accuracy and density. Because the analog clinical records 1 can have complex surface anatomy, each record typically requires multiple scans to digitize the entire relevant surface. A scan generally produces a single data file. The set of data files for an individual record forms a Scan Data Set for that record. All scanned data sets for a particular patient can be archived in a computer Data Storage Device 3 as Scan Data Sets 6. The Scan Data Sets for a particular patient comprise second part of the VDP Data Set 5 for that patient.

The multiple data files in a single Scan Data Set may be processed by the Process Data Sets Algorithms 7 to form a single data file that represents the relevant surfaces of the record. This process will be described in detail below. The processed file of a particular record forms a Record Data Set for that record. The Record Data Set may be archived in a Computer Storage Device 3 as one of the Record Data Sets 8. The Record Data Sets for a particular patient comprise a third part of the VDP Data Set 5 for that patient.

The Record Data Sets 8 and the Digital Data Sets 10 for a specific patient are processed to create 9 a virtual rendition of that patient. The processes of the various embodiments of the invention, which will be described in detail later in the description, produce several different data sets that orient the different records to each other and that control the motion of the lower jaw relative to the upper jaw. In some embodiments, these data sets may be archived as Create Data Sets 11 in the computer Data Storage Device 3. The Create Data Sets comprise the fourth component of the VDP Data Set.

In some embodiments of the invention, the VDP Data Set 5 that is created is archived in the VDP Data Sets 13. The VDP Data Sets are one part of the Computer Population Database 18, which can reside in a computer Data Storage Device 3. Along with the VDP Data Sets 13, Computer Population Database 18 includes two other data sets: the Parameter Data Sets 15 and the Population Data Set 17. The Parameter Data Sets 15 contain the changes with time of all the parameters that can be measured using the VDP Data Sets. Examples of these parameters are the wear of teeth, movement of teeth, changes in soft tissue, etc. These parameters will be described later in the description. The Population Data Set 17 comprises statistics on all of the parameters included in the Parameter Data Sets 15. The Statistical Analysis 16 is based on pooled data from all of the patients in the VDP Data Sets 13, and may be done for each parameter in the Parameter Data Sets 15.

The parameter change with time may be measured by comparing two VDP Data Sets 5 for the same patient made at two different time periods. The data sets may be selected from the VDP Data Sets 13 in the Computer Population Database 18. In some embodiments of the invention, the two data sets are fit to each other using the Fit Data Sets routines 12. The changes are calculated and archived in the Parameter Data Sets 15 using the Report Generator 14. A detailed description of the processes for fitting VDP data sets and calculating the changes in the parameters with time are provided later in the description.

Processing of the data sets, creating the VDPs, fitting VDP data sets, and report generating typically require the data sets to be rendered on a computer monitor for operator input. The rendering may be done using 3D Rendering Algorithms 19. Operator input is through the Rendering Tools 20, which manipulate the rendered image, and the Measurement Tools 21, which interact directly with the point data in the data sets. These tools will be described later in the description.

Figure 2:
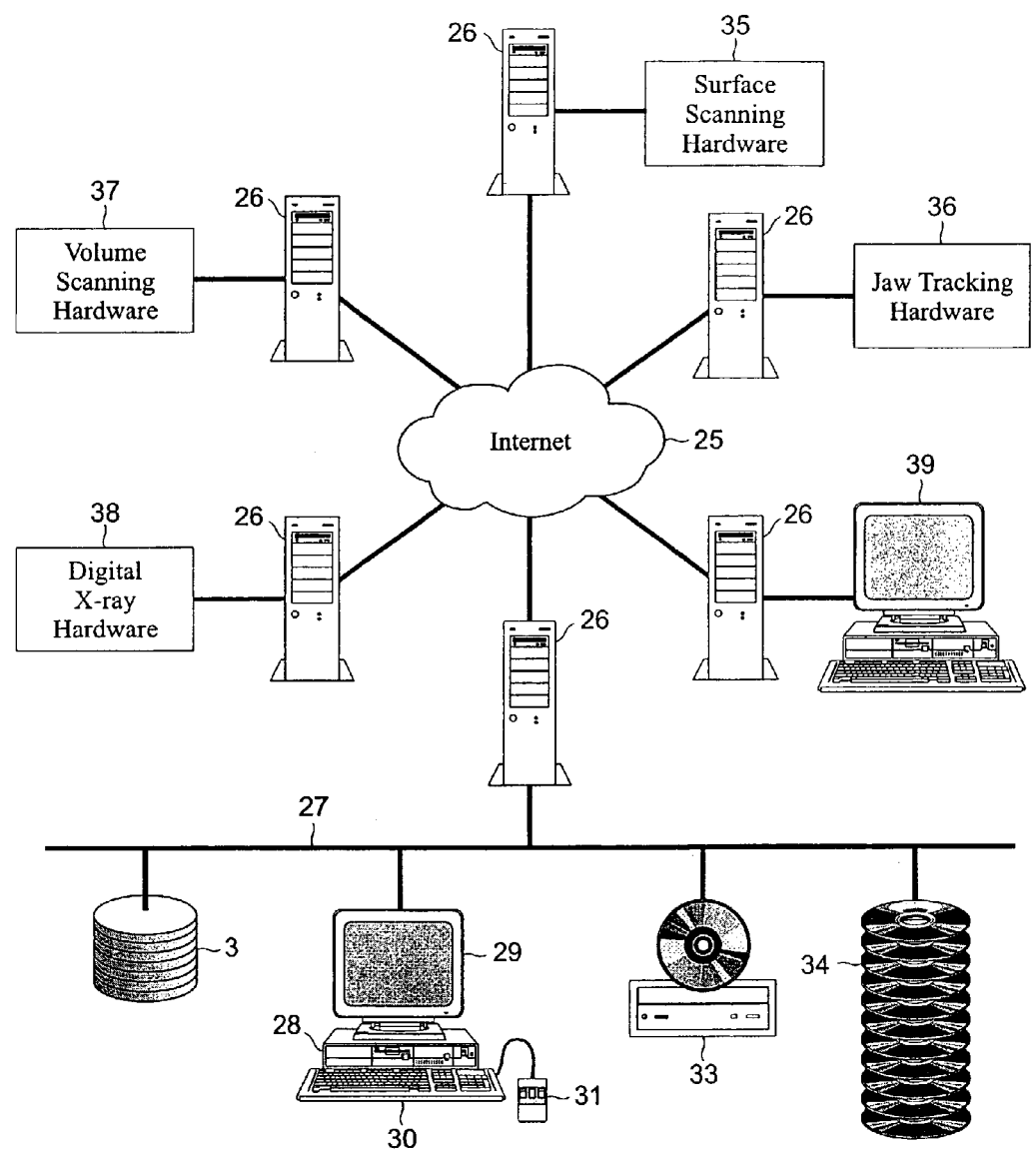
FIG. 2 is a diagram of a typical hardware configuration for implementing the processes of the present invention.

The present invention is not limited to any particular number or type of digitizing hardware or high-performance three-dimensional graphics hardware; however a typical example of such hardware is shown in FIG. 2. The embodiments of the invention are designed to benefit dentists and dental professionals throughout the world. Thus, it is desirable that the hardware for digitizing the clinical data be accessible throughout the world. Some embodiments of the invention make use of the Internet 25 for transferring the digital data from one site to another. Each hardware component may be connected to a network, such as the Internet 25 via a computer or server 26. Some or all of the hardware may be connected via a Local Area Network (LAN) 27. Additionally, some or all of the hardware may be connected to an intranet such as a corporate network.

As indicated in FIG. 1, the clinical data for the VDP takes the form of either Analog Clinical Records 1 or Digital Clinical Records 2. The Analog Clinical Records 1 comprise records of the patient made by the dentist or dental professional that are typically converted to a digital format using Surface Scanning Hardware 35. Examples of these records include, but are not limited to, impressions of the jaws, bite records, functional records, and conventional radiographs. Digital Clinical Records 2 comprise records that may be made directly by digitizing the patient. One example is Jaw Tracking Hardware 36 that directly measures the motion of the lower jaw relative to the upper. Any three-dimensional jaw tracking system that provides a path of distinct points selected on the lower jaw may be used; the present invention is not limited to any particular jaw tracking system. A second example is the Digital X-ray Hardware 38, which directly captures a radiograph in a standard digital format. Any conventional digital radiograph hardware may be used; the present invention is not limited to a particular type. A third example is the use of the Surface Scanning Hardware 35 to digitize the head and neck anatomy of the patient and the analog clinical records. A fourth example is Volume Scanning Hardware 37 that produces data sets describing the internal structures of the patient. Examples of the Volume Scanning Hardware 37 are Magnetic Resonance Imaging (MRI) and Computed Tomography (CT). It should be noted that the above-described examples can be used in any combination; the embodiments of the invention do not require all or any particular combination of the examples.

The hardware used to construct the VDP Data Sets 5 (FIG. 1) and manage the Computer Population Database 18 (FIG. 1) may be connected via a LAN 27. The processing of the data sets is typically done using a computer 28 that has input devices such as a keyboard 30 and mouse 31 and a monitor 29. The computer is connected to the Data Storage Device 32, which is diagrammed as located externally to the computer on the LAN 27; however, it may also be located in the computer 28, or even at a different site, connected through the a network such as a LAN or the Internet. Also illustrated are a CD writer 33 that may be used to make backups of the data stored in the Computer Population Database 31 and a CD jukebox 34 to provide the ability to conveniently archive data sets. Although some embodiments make use of CDs for storage of data, any storage method could be used.

In some embodiments, access to the VDP software and Computer Population Database may be made available to dentists, dental professionals, and qualified third parties that have a suitably configured computer system. This configuration of hardware enables a central storage of the VDP data, continuous updating of the Population Data Set 18 (FIG. 1), and access to data by all qualified users irrespective of their location.

Figure 3:
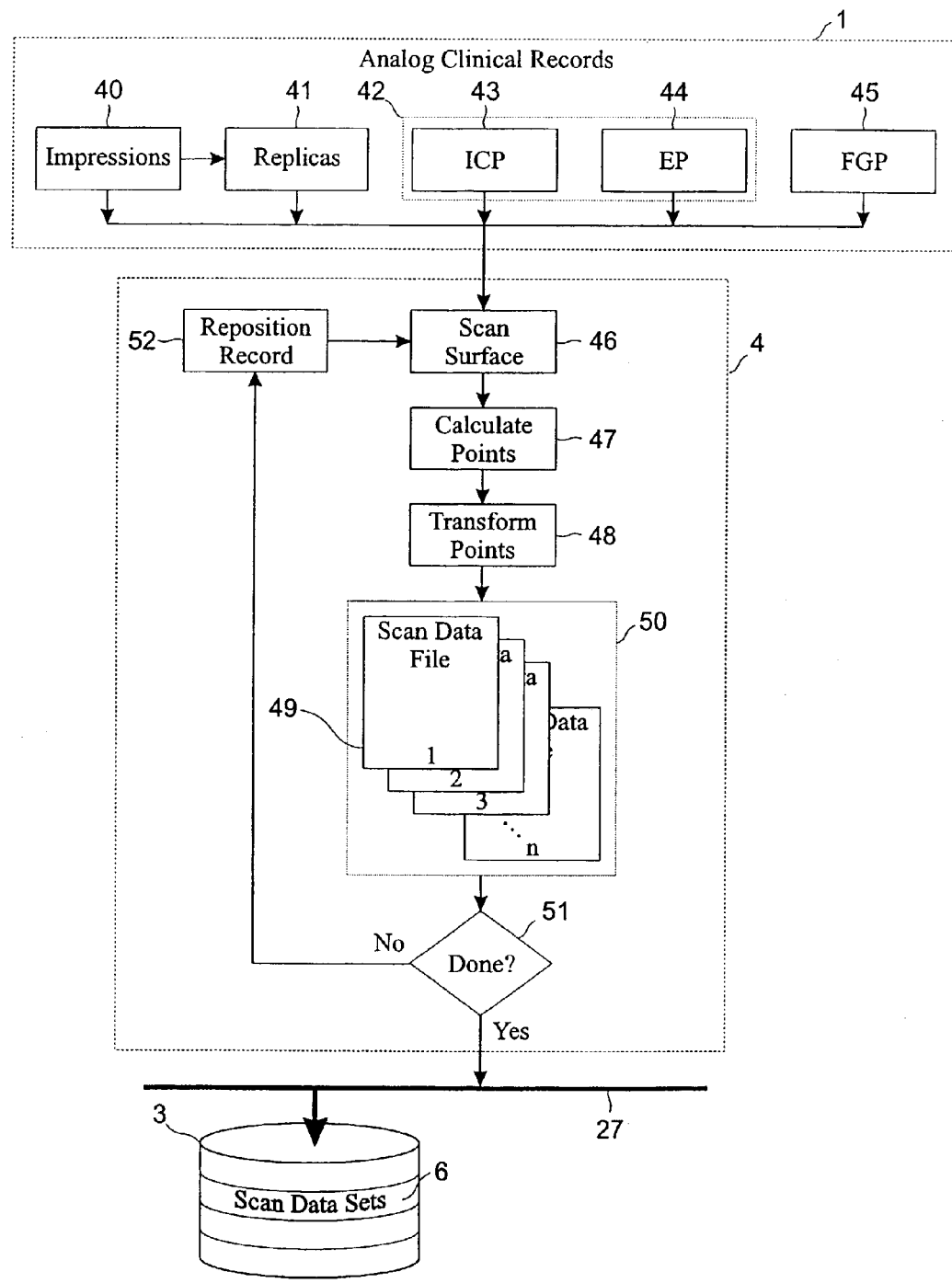
FIG. 3 is a block diagram illustrating in more detail the general order of flow of FIG. 1 for scanning the analog clinical records.

FIG. 3 is a block diagram illustrating in more detail the general order of flow for the Scan Records process 4 used in some embodiments of the invention to scan the Analog Clinical Records 1. Included in the types of clinical records that typically involve surface scanning are the four records types shown: Impressions 40, Replicas 41, Bite Registrations 42, which includes the Intercuspal Position (ICP) and Excursive Position (EP) records, and Functionally Generated Path (FGP) Records 45. The dentist or dental professional typically makes each of these records that capture the patient's dental state at a particular time.

The impressions 40 capture the surface anatomy of the patient's jaws, which normally includes all teeth that are present and the surrounding soft tissues of the jaw. Any suitable impression material, such as addition silicones, may be used. The Replicas 41 of the impressions are casts made by pouring a replicating material into the impressions. Any material may be used that is stable, compatible with the scanning hardware, and that forms an accurate reproduction of the impression. Examples of the replicating materials include but are not limited to dental stones and dental die epoxies.

Some embodiments include two types of Bite Registration Records 42: the ICP 43 and the EP 44. Generally they differ only in the positions of the teeth at the time the record is made. The intercuspal position occurs when the jaws are as close together as possible and the teeth have their maximum intercuspation. The excursive position occurs when the teeth are in a position other than the ICP, but still in contact. The ICP and EP bite records may be made clinically using any of a number of different types of registration materials; however, addition silicones are a typically used material. A method of making these records will be discussed later in the description.

A fourth type of clinical record used in some embodiments of the invention is the Functionally Generated Path (FGP) record 45, which records the movements of the lower jaw relative to the upper jaw while the teeth are in contact. Some embodiments of the invention use a thermoplastic material known as Easy Tray from SDS Kerr to capture the path of movement. A method of making a FGP record will be discussed later in the description.

Each of these clinical records may be scanned using Surface Scanning Hardware 35 (FIG. 2) to produce a set of coordinate points that represent the surface anatomy of the record. Some embodiments of this invention use scanning hardware that is connected to a LAN 27; however, as indicated in FIG. 2, the scanning hardware may be located anywhere. In addition, some embodiments of the use an optical digitizer to scan the clinical records; however, any 3D digitizing system may be used that produces point data with suitable accuracy and point density. An example of such a scanner is the Comet 100 optical digitizer. An Analog Clinical Record 40, 41, 43, 44, or 45 is mounted in the scanner. In some embodiments, the following operations may be carried out by the scanning system hardware and software: Scan Surface 46, Calculate Points 47, Transform Points 48 to a common coordinate system, then create a Scan Data File 49. Because of the complex surface anatomy of the records, the record normally involves scanning from different orientations in the scanner, therefore it may be necessary to Reposition the Record 52 and perform another scan. Each scan has at least one Scan Data File 49, which may be stored on the scanning system's computer. The complete set of Scan Data Files 49 forms a Scan Data Set 50. This process may be repeated until the entire surface of the record is scanned 51. In one embodiment of the invention, the Scan Data Set 50 is archived in the Scan Data Sets Section 6 of the Data Storage Device 3. The data transfer as illustrated may be done either over a LAN 27 or the Ethernet as depicted in FIG. 2. Although electronic transfer of the data is desirable, the data files can be transferred using other methods. For example, the data files may be stored on a removable disk such as a floppy disk, CD-ROM, or DVD-ROM and transported to another system for further processing.

Figure 4:
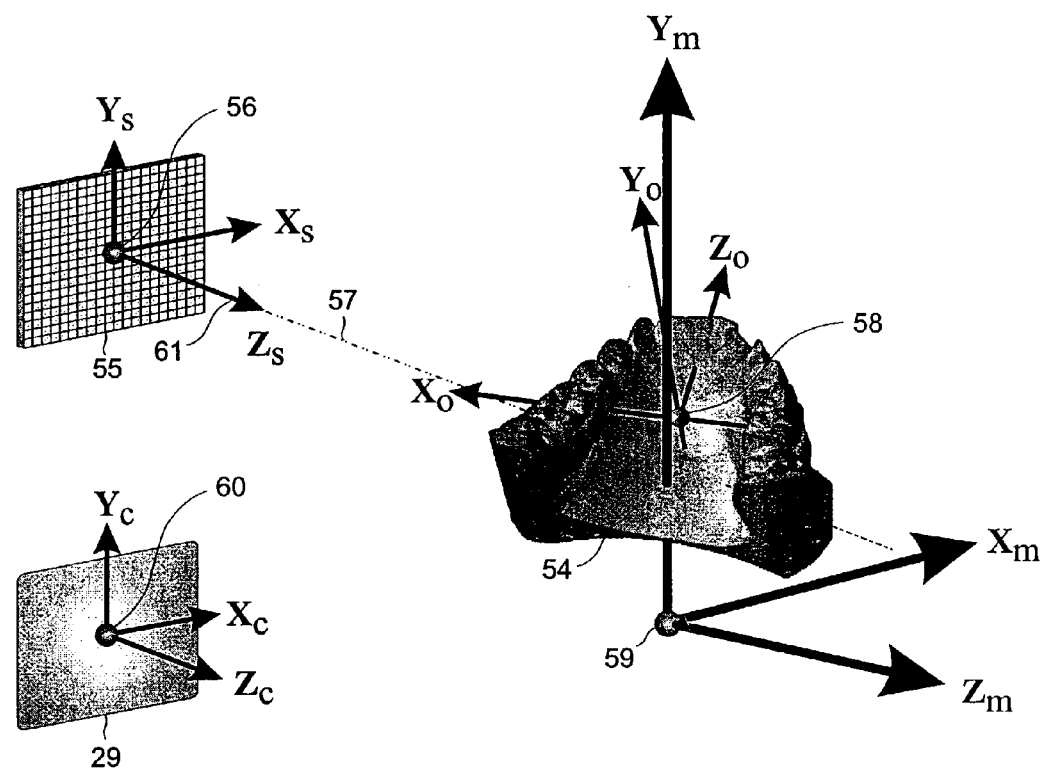
FIG. 4 is a schematic diagram representing the four coordinates systems used in the present invention.

FIG. 4 is a schematic diagram representing the four coordinate systems used in various embodiments of the invention. In one embodiment of the invention, each scan of the Analog Clinical Record 54, which is represented in FIG. 4 by the replica cast of the lower jaw, captures a single view of the record using a Charged Coupled Device (CCD) 55. This device has a coordinate system 56 with its Z-axis 61 typically directed parallel to the line of sight 57 of the camera containing the CCD. The clinical record 54 typically has its own coordinate system 58, whose orientation may be independent of the CCD coordinate system 56. The scanning system has coordinate system 59 that is typically fixed in space. The scanning system coordinate system 59 may be mechanically linked to the CCD coordinate system 55 and to the Record coordinate system 58 through the translation and rotation tables of the scanner. Transformations between these three coordinates systems 55, 58, and 59 are possible based on the geometry of the scanner and the relative movement of the CCD 56 and the Record 54 in the scanner. The fourth coordinate system 60 is that of computer monitor 29. Its Z-axis 62 is typically perpendicular to the monitor screen 29. As those of skill in the art will appreciate, scanners other than those with CCD devices can be used, and are within the scope of the invention. Moreover, the orientation of the coordinate systems described above can vary; those of skill in the art will recognize the appropriate transformations to apply in these coordinate systems.

Figure 5:
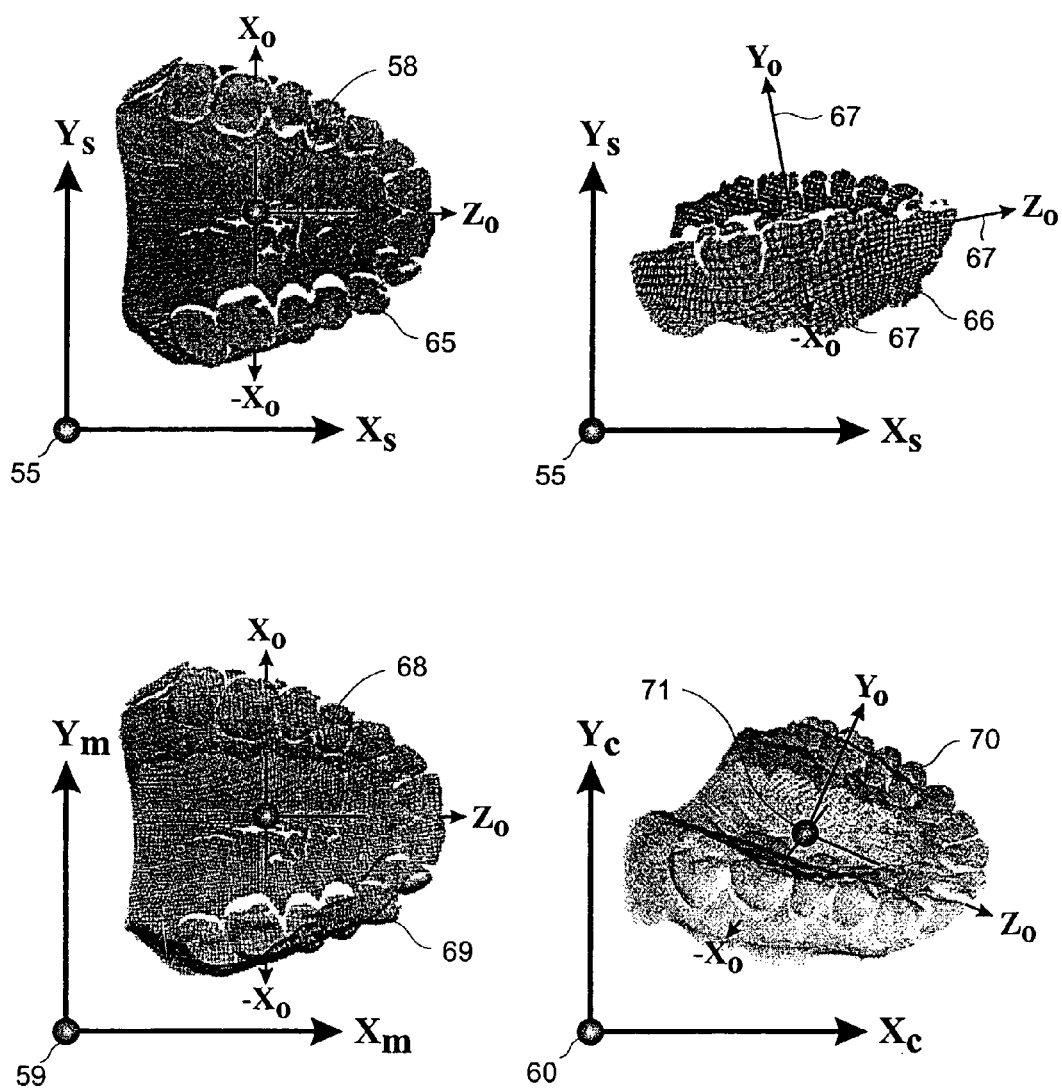
FIG. 5 is a schematic diagram illustrating the relationship between scanned data sets and coordinate systems.

FIG. 5 is a 2D illustration of the relation between the point data sets and the coordinate systems according to an embodiment of the invention. Data sets 65 and 66 are two sets of exemplary (x,y,z) coordinate points obtained by scanning a replica of an upper jaw from two orientations in a Comet 100 scanner. Point coordinates were calculated in the CCD coordinate system 55 (the Z-axis points out from the plane of the paper) of the scanner. Because the orientations of the body coordinate system 58 and 67 are different, a transformation is involved to align the scan data files 65 and 66. Transformation of the data sets 65 and 66 to the scanner coordinate system 59 (the Z-axis points out from the plane of the paper) may be based on the rotation and translation values of the scanning hardware used to position the replica. Transforming the body coordinate systems 58 and 67 to the same orientation 68 in the scanner coordinate system 59 aligns the two point data sets 69. The transformed data files may be stored in the Scan Data Sets 6 (FIG. 3). The aligned data sets 70 are shown in the computer monitor coordinate system 60 (the Z-axis points out from the plane of the paper) with a new orientation for the body coordinate system 71 based on user input. The image of the point data rendered on the computer monitor is called a point cloud.

Figure 6:
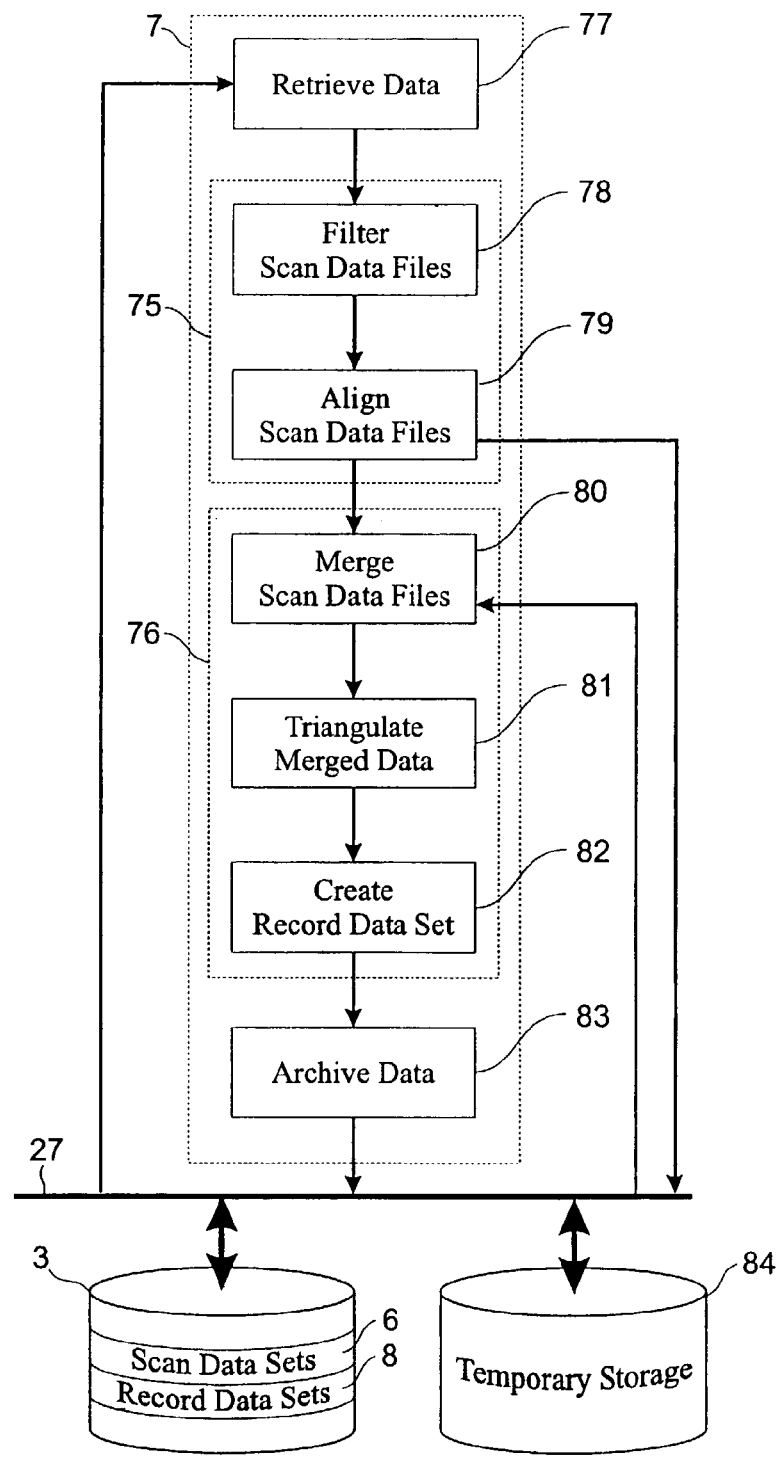
FIG. 6 is a block diagram illustrating the general order of flow to process the scan data sets in accordance with an embodiment of the present invention.

In some embodiments, the scanned data from the analog clinical records are processed to a VDP format. FIG. 6 is a block diagram illustrating the general order of flow of a method to process the Scan Data Sets in accordance with an embodiment of the present invention. The Scan Data Sets 6 for objects scanned using the scanning hardware are processed 7 into Record Data Sets 8. As illustrated in FIG. 3, each Scan Data Set 50 typically contains a set of Scan Data Files 49, which may be stored on the computer storage device 3. The execution of the method of process 7 is desirable in order to improve the quality of the data, merge the data into a single file, provide a surface to the point data, and archive the data.

In some embodiments, retrieve Scan Data Set component 77 contains routines that retrieve a Scan Data Set 6 from the computer storage device 3 and output point data contained in the Scan Data Files of the data set. The Filter Data Files component 78 includes routines to improve the quality of the data. Files are typically filtered individually. Filtering includes, but is not limited to, routines that remove bad data points, smooth the data, delete border points, and calculate surface normals. In some embodiments of the invention, alignment of the scanned data in the individual data files is improved by Align Data Files component 79 routines that identify and minimize the distance between points that represent the same area of the scanned object. The filtered and realigned Scan Data Files may be merged to a single data file by routines in the Merge Data Files component 80. Routines in the Triangulate Merged Data component 81 triangulate the point data in the merged data file. The triangle information may then be used to apply a surface to the point cloud. The Create Record Data Set component 82 contains routines that organize the results of the merging and triangulation process into the VDP Record Data Set 8, which can be archived in the computer storage device 3 by routines in the Archive Data component 83. Data retrieval 77 and archiving 83 are illustrated using a LAN 27; however, other file transfer methods can be used and are within the scope of the present invention.

The filtering and alignment processes 75 may use either custom algorithms or proprietary software available independently. Examples of such software include PolyWorks (from InnovMETRIC Software) or software packaged with the scanning system. The merging, triangulation, and formatting processes 76 are further described below. In some embodiments, the filtered and aligned data files may be stored temporarily on a computer hard drive 84 for use later by the merging routines. Although the temporary files are illustrated as existing on the LAN 27, they could be located in the processing computer or elsewhere on a system communicably coupled to the processing computer, for example, via a LAN or the Internet.

Figure 7:
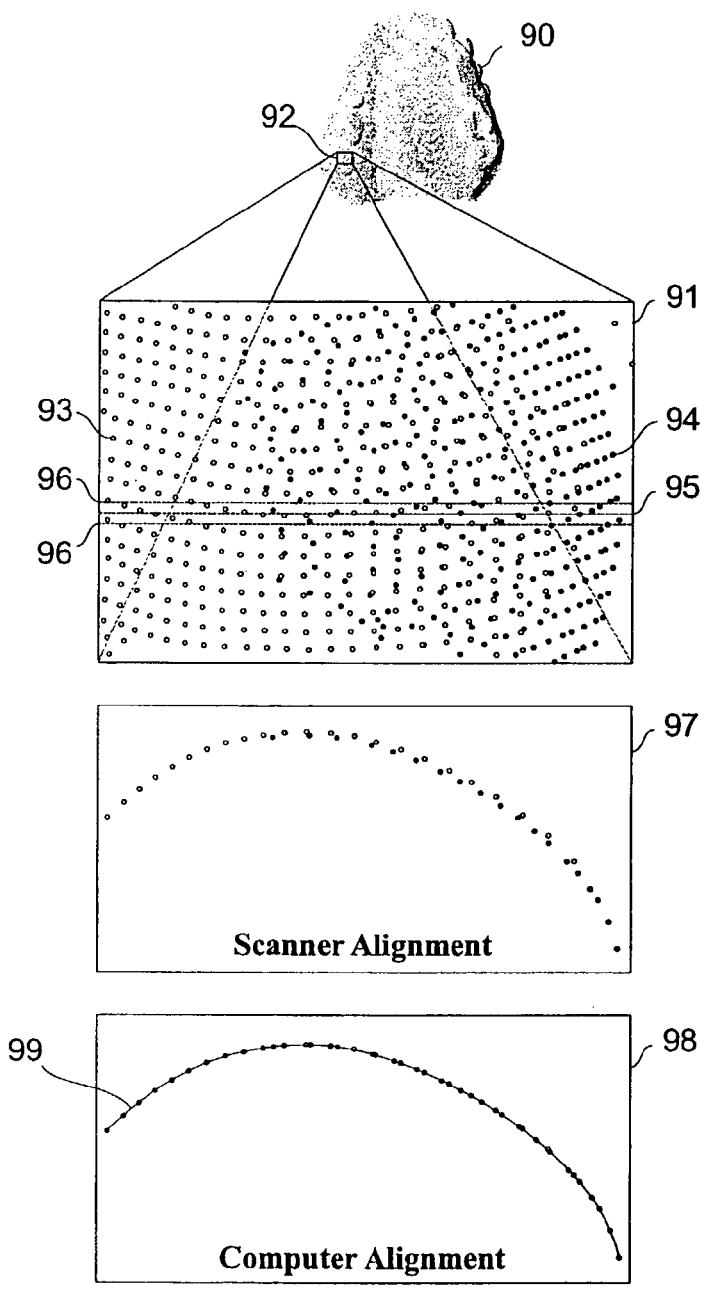
FIG. 7 is a schematic diagram illustrating the improved alignment of scanned data resulting from the use of computer routines.

FIG. 7 schematically illustrates the improvement that may be gained in embodiments of the invention using computer optimization to align points in the scan data files. The scan data files 65 and 66 of FIG. 5 are shown in jaw image 90 as aligned by the scanner hardware and software. For clarity, the outlined region 92 of image 90 is expanded in box 91 to show the points. Points in scan data files 65 and 66 are represented by open circles 93 and filled circles 94, respectively. The improved alignment is better illustrated by viewing a cross section through the point cloud at location 95. Because the points do not fall on a regular grid it is desirable to include in the cross section view all of the points that are with a defined distance of location 95, which is represented by the two lines 96 parallel to location 95. The resulting cross section 97 may first be aligned by the scanner hardware and software. Cross section 98 is the result of computer optimization of the alignment. Line 99 is a best fit to both sets of points and represents the surface contour. The computer alignment normally reduces the root mean squared difference between the points in the data sets by a factor of two or more.

Figure 8:
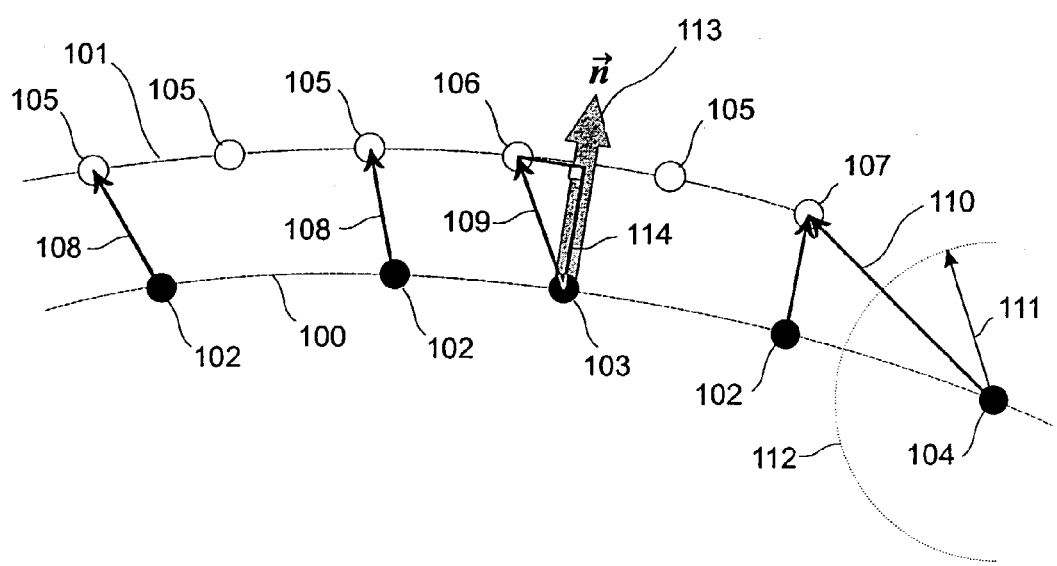
FIG. 8 is a schematic illustration of the method for aligning two sets of scan data.

Some embodiments of the invention employ computer optimization to minimize the distance between the surfaces that represent the data sets. FIG. 8 is a schematic illustration of a method according to an embodiment of the invention for aligning two sets of scan data. Lines 100 and 101 represent a cross section of two scanned surfaces at a location of overlap. The filled circles (102, 103, and 104) and the open circles (105, 106, and 107) are the calculated surface points for surfaces 100 and 101, respectively. The arrows (108, 109, 110) point to the closest point (nearest neighbor) on surface 101 to the selected point on surface 100. In some embodiments only points with a nearest neighbor distance less than a predefined distance 111 are considered in the optimization. For example, point 104 has the nearest neighbor 107. The distance between the two points 110 is greater than the predefined distance indicated by the arc 112, which has a radius equal to predefined distance 111. Thus point 104 is not included in the optimization calculations.

The optimized parameter is the distance from surface 100 to surface 101 from all points on 100 that have nearest neighbor distances less than the predefined distance 111. The distance from a selected point 103 on surface 100 to the surface 101 can be approximated either as the nearest neighbor distance 109 or the distance obtained by projecting the nearest neighbor distance 109 on to the surface normal 113 at point 103. The projected distance 114 is the estimate for the distance from point 103 to the surface 101.

Figure 9:
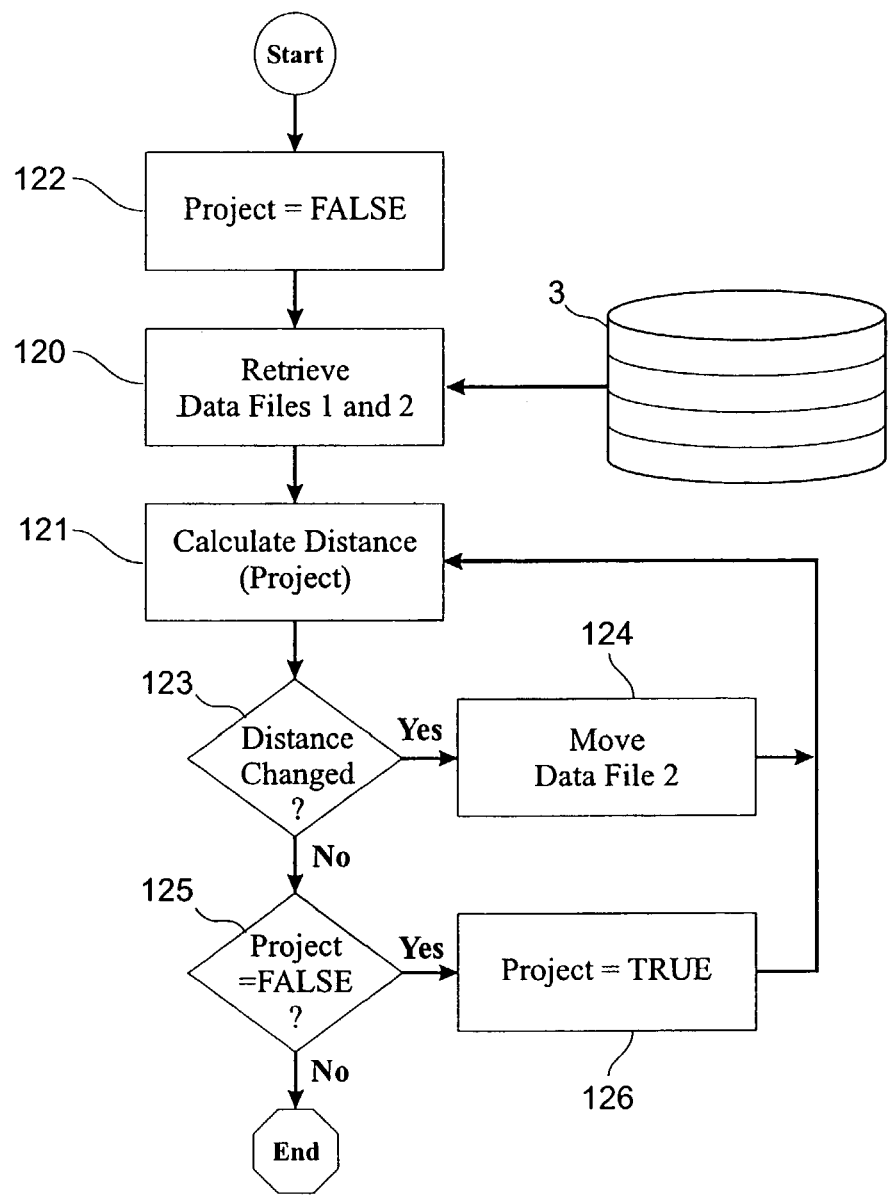
FIG. 9 is an illustration of the flow diagram for the computer optimization routines used to align two data files.
Figure 10:
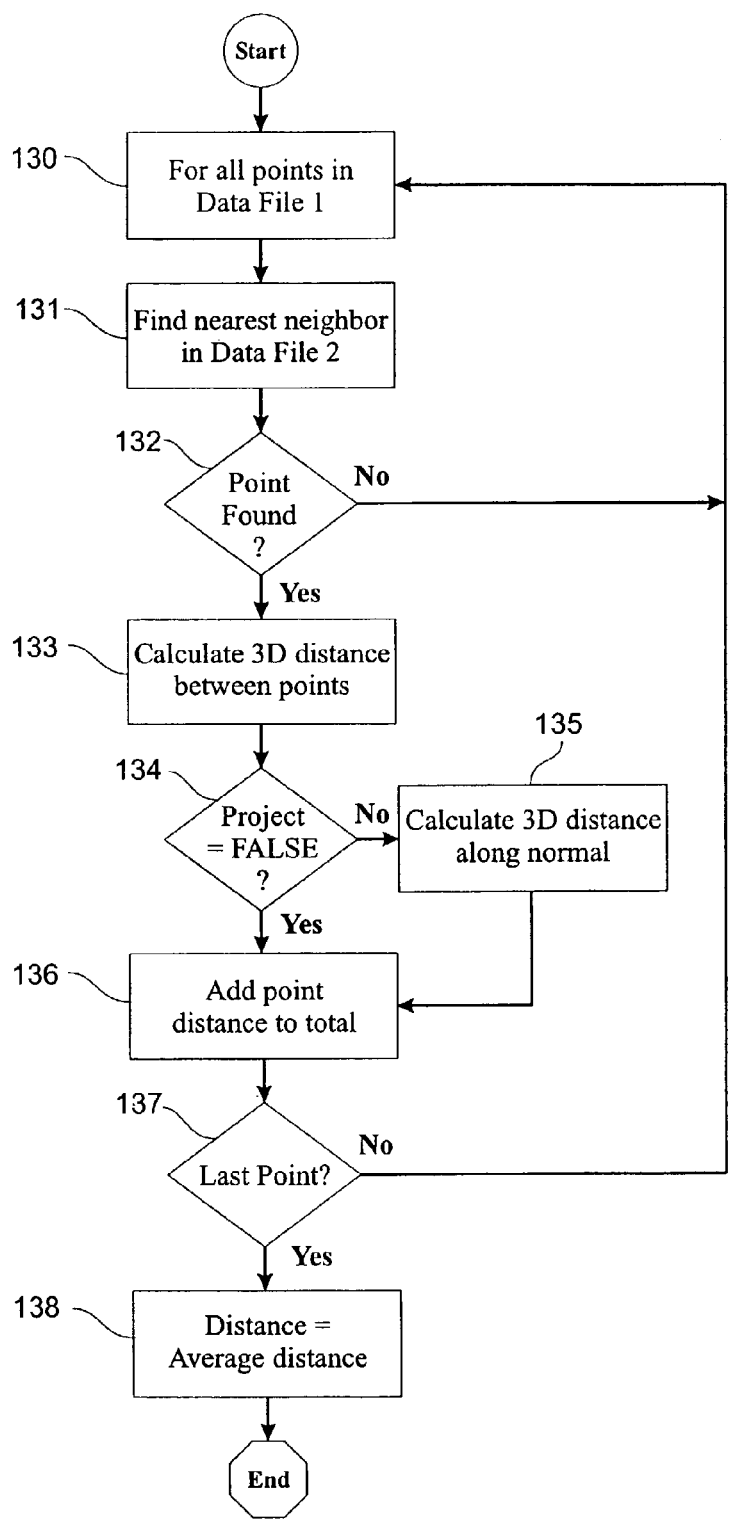
FIG. 10 is an illustration of the flow diagrams for calculating the distance between two point data sets.

A method according to an embodiment of the invention that performs computer optimization algorithms that minimize the distance between surface 101 and 100 is illustrated in FIG. 9 and FIG. 10. Data retrieval routines 120 acquire two data files from the computer storage device 3. The distance between points in the two data files is calculated by the Calculate Distance routines 121. In some embodiments, how the distance is calculated depends on the value of Project attribute 122. If the new value for distance has changed from the previous value 123, then the optimization algorithm 124 transforms the points in the second data file to a new location, and the process is repeated. This continues until the change in the distance parameter is less than a predefined tolerance. If the value of Project is "FALSE" 125, then the value of Project is changed to "TRUE" 126, and the process is repeated a second time using the projection method (FIG. 8) for calculating the distance parameter; otherwise the process stops. In one embodiment of the invention, the optimization process 124 uses the Simplex algorithm known in the art; however, any robust optimizing algorithm could be used.

A method for calculating the distance according to various embodiments of the invention is illustrated the flow diagram in FIG. 10. The distance algorithm uses a "for loop" to select a point, $p_i$, in the first data file 130. An octtree search algorithm finds the point in the second data file that is closest to $p_i$, and is within a predefined distance of that point 131. If no point is found 132, a new point, $p_{i+1}$ is selected from the first data file; otherwise, the 3D distance between the two points is calculated 133. If the variable Project is TRUE 134, the 3D distance is projected onto the surface normal for $p_i$ 135. A running total 136 is kept of the distance until all points have been considered 137. The returned value for the distance is the average distance 138.

Figure 11:
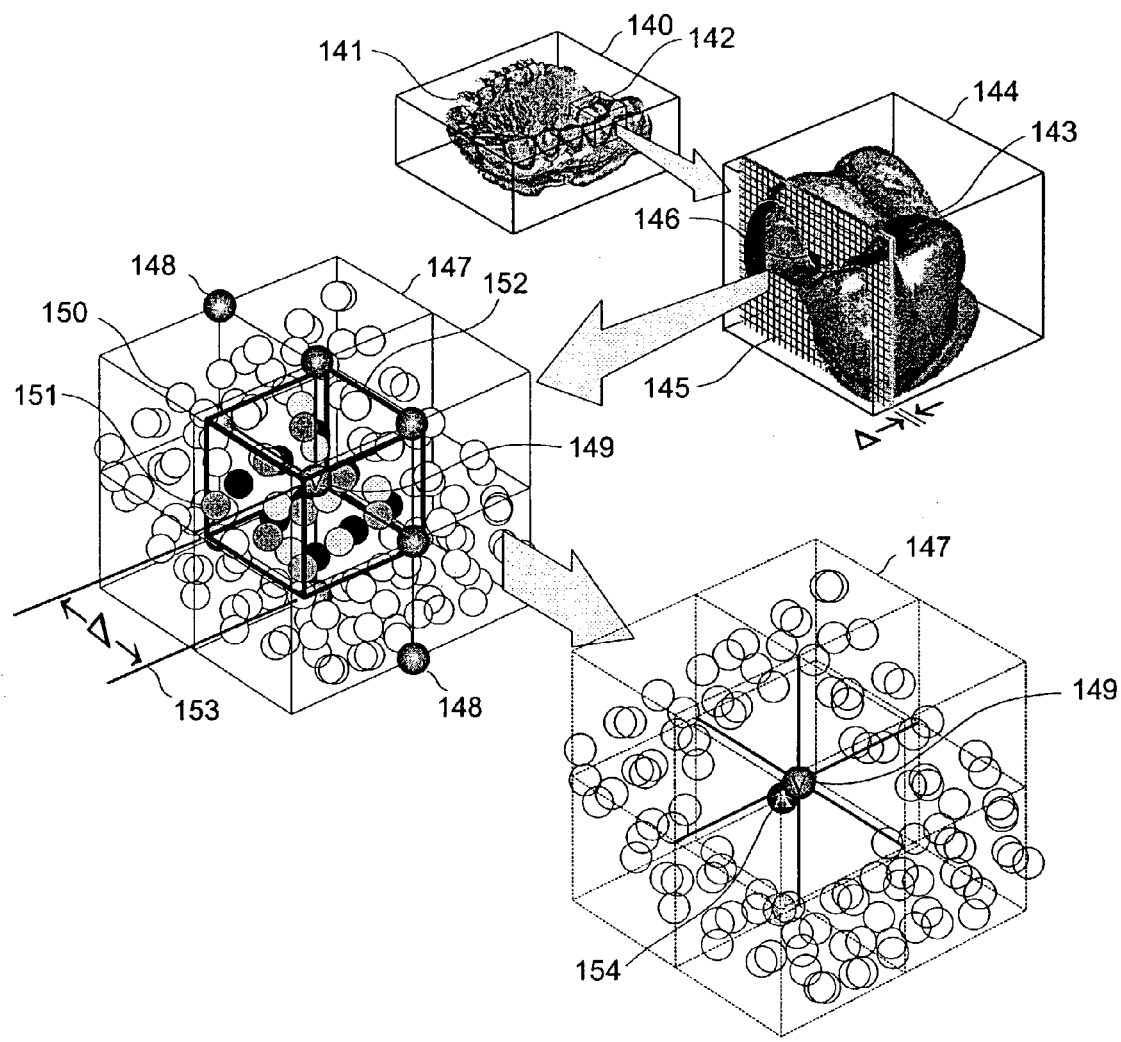
FIG. 11 is a schematic diagram illustrating the process of merging the multiple scan data files into a single data file.
Figure 12:
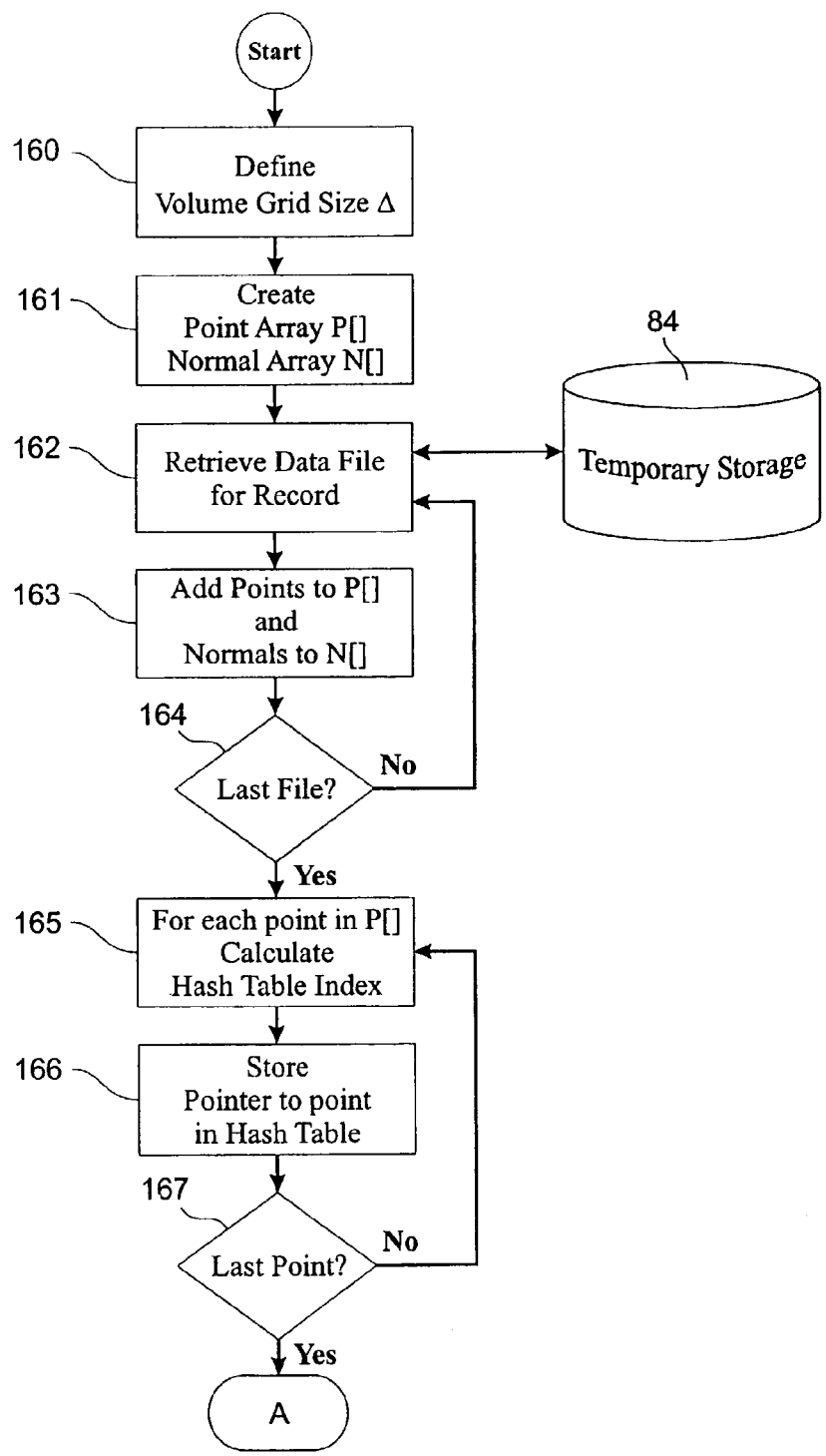
FIG. 12 is an illustration of the flow diagram for the computer routines used to create the hash table for merging the filtered and aligned data files into a single data file.
Figure 13:
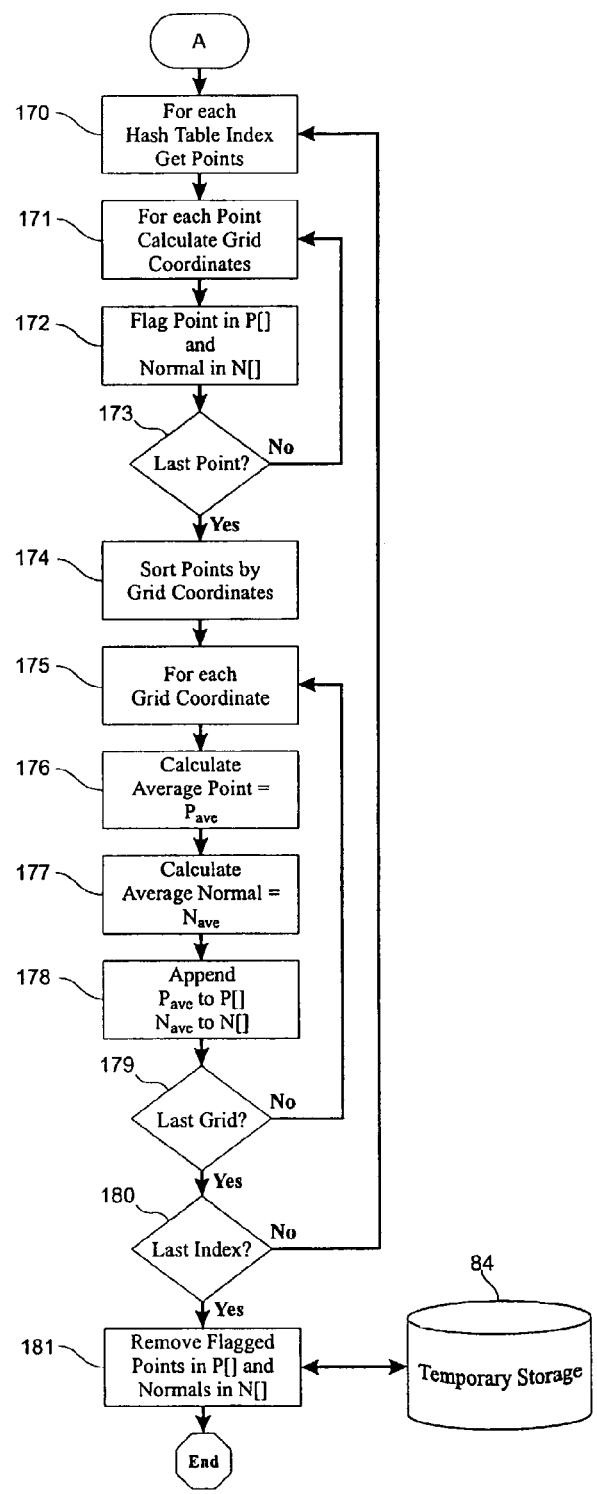
FIG. 13 is an illustration of the flow diagram for the computer processing of the hash table points into an array of averaged points and normals.

A method for merging the aligned data files into a single data file according to an embodiment of the invention is illustrated in FIG. 11, and in the flow diagrams of FIG. 12 and FIG. 13. The rectangular space 140 containing the digitized image of the object 141, which is represented in FIG. 11 as an upper jaw, is subdivided by a regular 3D grid. For clarity, the cubic volume 142 surrounding a molar tooth 143 is expanded in cube 144. The volume slice 145 through the molar image 143 illustrates one segment of the grid that subdivides the volume 144. The grid spacing is A along all three axes. The highlighted region 146 on the front plane of the volume slice 145 is expanded in cube 147 to show the nine grid coordinates 148 and 149 contained in the highlighted region. Also shown are the surface data points, indicated by open 150 and shaded 151 circles that lie within the grid coordinates located on either side of the highlighted region 146. The merging process associates each surface point with the closest grid coordinate. For example, all surface points 151 in the cube 152, which has a side length of size Δ 153 and is centered on grid coordinate 149, are associated with grid coordinate 149. The points 151 are averaged to obtain a single point 154 that is linked to grid coordinate 149. The process is repeated until all of the surface points that make up the object have been considered. Besides merging the multiple databases into a single file, the merging process also reduces the number of surface points and reestablishes a grid-like structure to the data.

FIG. 12 is an illustration of a flow diagram for computer routines that create a hash table used in some embodiments of the invention to merge the aligned data files into a single data file. In some embodiments, the grid interval Δ is set to be the mean distance between adjacent surface data points 160. Some embodiments allow the user to change this value. Two arrays P[ ] and N[ ] are defined 161: P[ ] holds the (x,y,z) coordinates of all the scanned points, and N[ ] holds the (x,y,z) coordinates of the corresponding normals. The array indices for the point and its normal are the same. Each scan data file for the selected analog record is retrieved 162 from the temporary storage device 84. The coordinates of the points and normals are added to the appropriate arrays 163. This continues until all of the files have been retrieved and all points and normals have been stored in the arrays 164. For each point in P[ ], a hash table index is calculated 165 and the array index for the point is stored in the hash table 166. The process continues through the last point in P[ ] 167.

FIG. 13 illustrates a flow diagram for a method according to an embodiment of the invention for computer processing of the hash table points into an array of averaged points and normals, i.e. the merged data. The points associated with a hash table index are retrieved 170. The grid coordinates are calculated for each point by dividing the x, y, and z coordinates of the point by Δ and rounding the results 171. The array index to the point in P[ ] is flagged 172. The process is repeated 173 for all of the points associated with the hash table index. The points are sorted by grid coordinates 174, then for each grid coordinate 175, all the points that have the same grid coordinate are averaged 176. An average normal is calculated from the normals of the points that were averaged 177. The average point and average normal are appended 178 to the P[ ] and N[ ] arrays, respectively. The process is repeated for all of the grid coordinates associated with the hash table index 179 and for all of the hash table indices 180. The flagged indices of the P[ ] and N[ ] arrays are deleted 181 and the results are stored in temporary storage 84.

Figure 14:
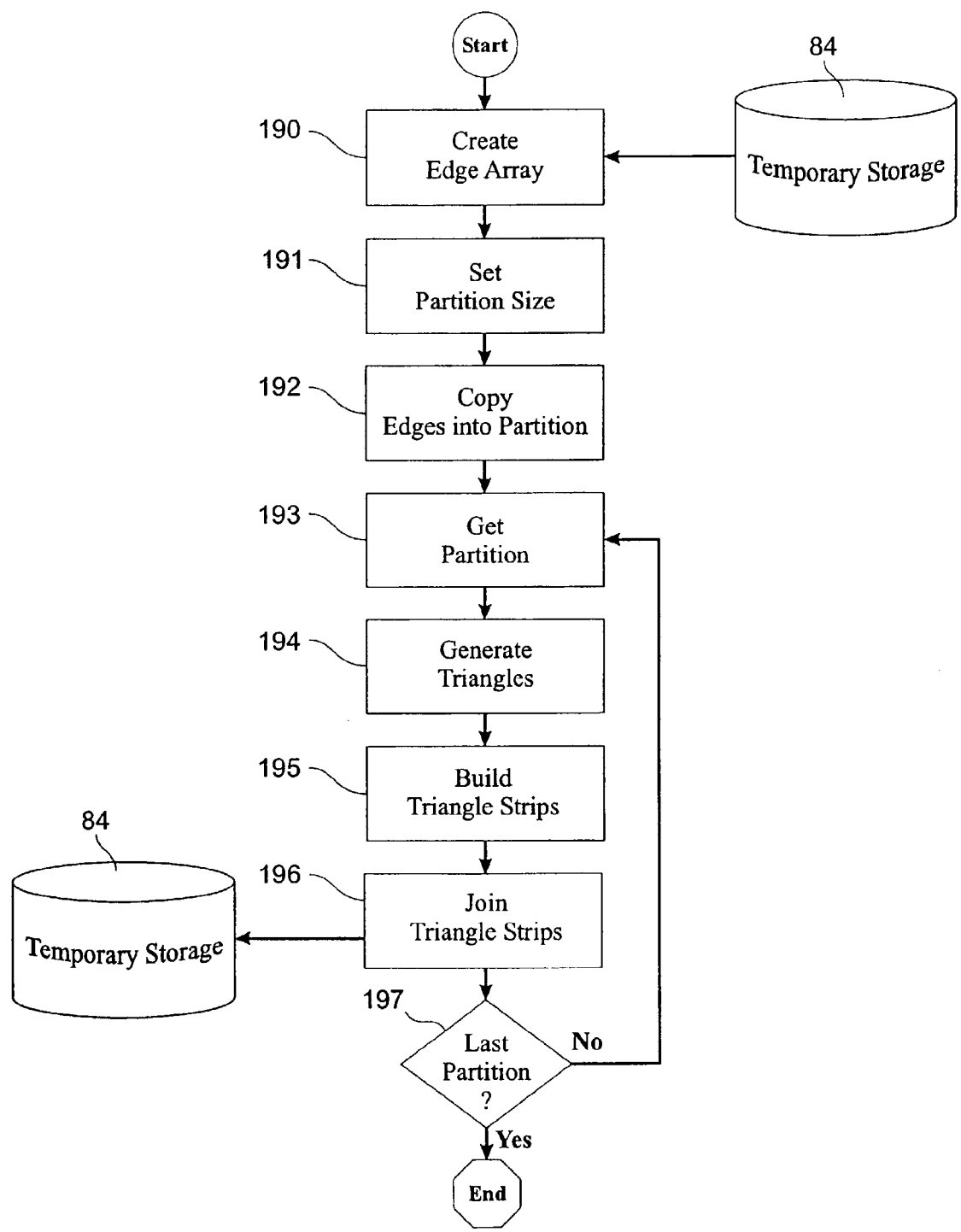
FIG. 14 is a flow diagram illustrating the computer process used to form triangles based on the averaged point data.
Figure 15:
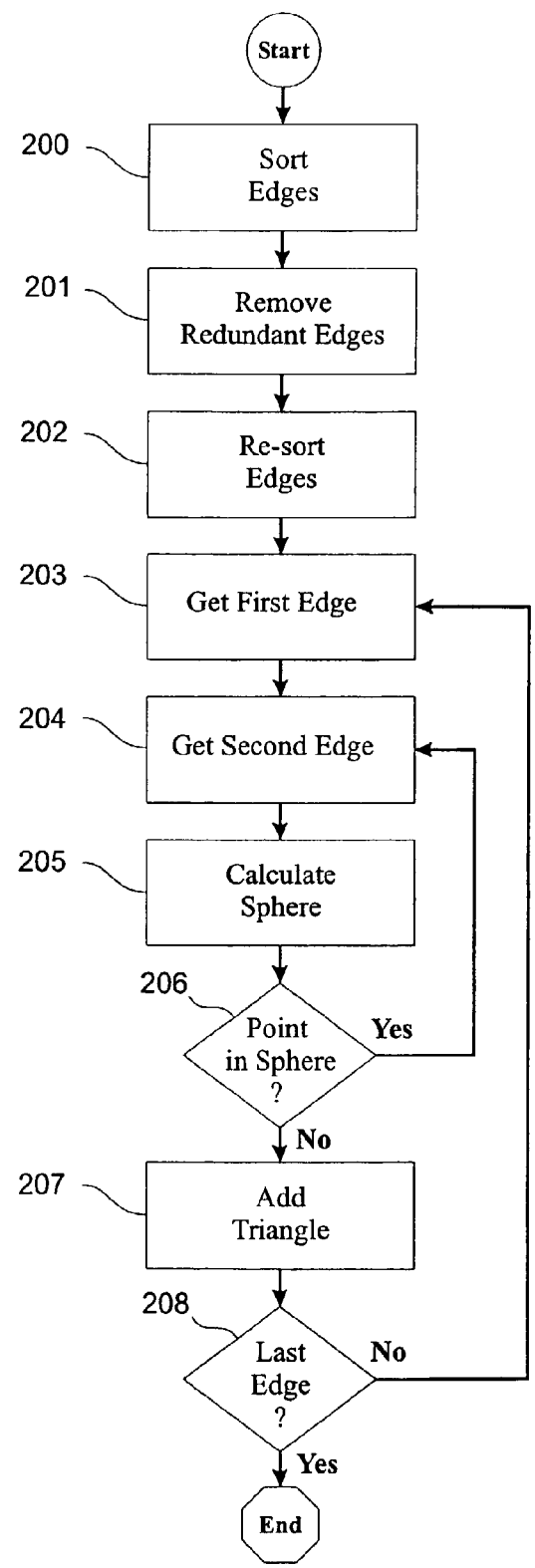
FIG. 15 is a flow diagram illustrating in greater detail the flow of the computer processes in the computer routine Generate Triangles of FIG. 14.
Figure 16:
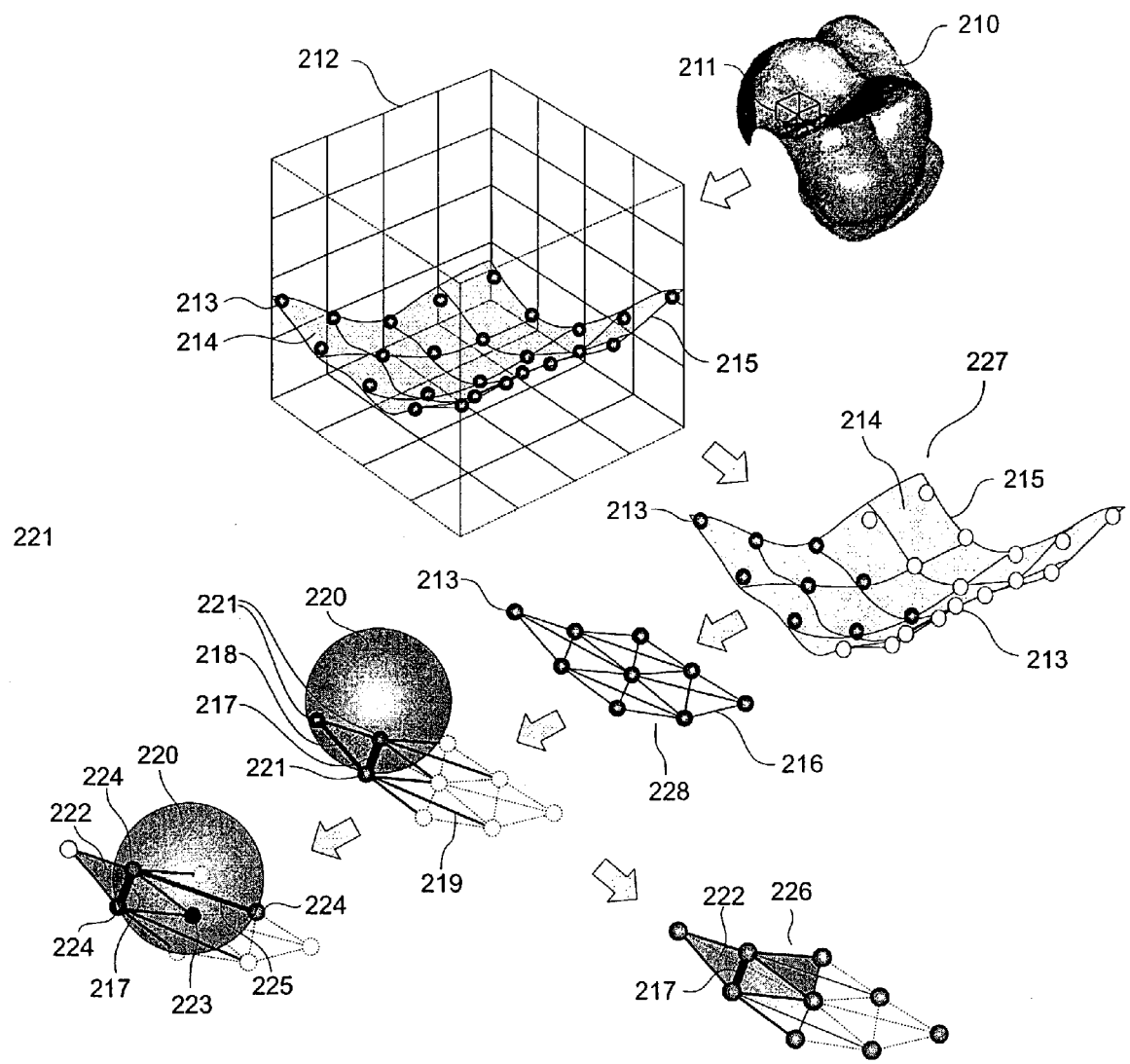
FIG. 16 is a schematic diagram illustrating the process of forming triangles from the averaged point data.

A method according to an embodiment of the invention to form triangles from the averaged data is illustrated in FIG. 14, FIG. 15, and FIG. 16. FIG. 14 illustrates the flow of the computer routines that triangulate the averaged data. An edge array is created 190 that contains all of the edges that can be drawn between adjacent averaged points. The volume that contains all of the averaged points is divided into partitions 191. One embodiment uses 5×5×5 partitions; however, any size partition can be used. The edges are copied from the edge array into the appropriate partition 192. For each partition 193, triangles are generated 194 using all the edges contained in the partition. This process is illustrated in more detail in FIG. 15, and is described below. Once the triangles are generated, adjacent triangles are linked to form triangle strips 195. Finally, the strips are joined 196. This process is repeated for every partition. At the completion of the process, the entire array of averaged points will be triangulated.

A method according to an embodiment of the invention for a computer process for generating the triangles is illustrated in FIG. 15. The edges in the partition are sorted 200 by the edge indices and any redundant edges are removed 201. The edge array is re-sorted 202. The first edge in the partition edge array is selected 203. A second edge is found 204 in the partition edge array that has a common edge index with either indices of the first edge. The coordinates of the center of a sphere with a fixed radius are calculated using the three endpoints of the two edges 205. The radius of the sphere is adjustable; however, in one embodiment, the radius is set to the mean distance between adjacent points. A test is done to determine if any of the other averaged points in the partition are located within the sphere. If no point is found 206, the triangle formed by the two edges is added to the triangle list 207; otherwise, no triangle is formed and a new edge is selected 204. This process is repeated until all of the edges that have a common index with one of the first edge indices have been tested 208. Next, a new edge is selected 203 and the process is repeated until all of the edges have been tested.

A schematic diagram for an exemplary method for the triangle forming process is illustrated in FIG. 16 for a point cloud of a tooth 210. A 5×5×5 partition 211 is shown in an expanded view 212. As noted above, the size of the partition can vary in alternative embodiments of the invention. The circles 213 represent the averaged points. The shaded area 214 represents the surface contained in the partition 212. The curved lines 215 represent the surface contour at the intersection of the surface with the cubes contained in the partition. The averaged points 213, surface 214, and contour lines 215 are redrawn in surface 227. The area in 227 indicated with the dark colored average points is redrawn in mesh 228 with all the partition edges 216, which are indicated by straight lines, for this segment. One edge 217 is selected from the array of edges. A second edge 218 is selected that has a common edge index with the first edge. The solid black lines 219 indicate edges with a common index to the first edge. A sphere 220 with a fixed radius is fit to the three points 221 that define the two edges 217 and 218. If no other average points are found within the sphere, a triangle 222 is created. If a point is found, as illustrated by the point 223 located in the sphere 220 positioned on the three points 224 defined by the two edges 217 and 225, then no triangle is created. The process is repeated for all of the edges 219 with a common index to the first edge 217. The resulting triangles for the first edge 217 are shown in illustration 226. A new edge is selected from the array of edges in the partition and the process is repeated until all of the edges have been tested.

Figure 17:
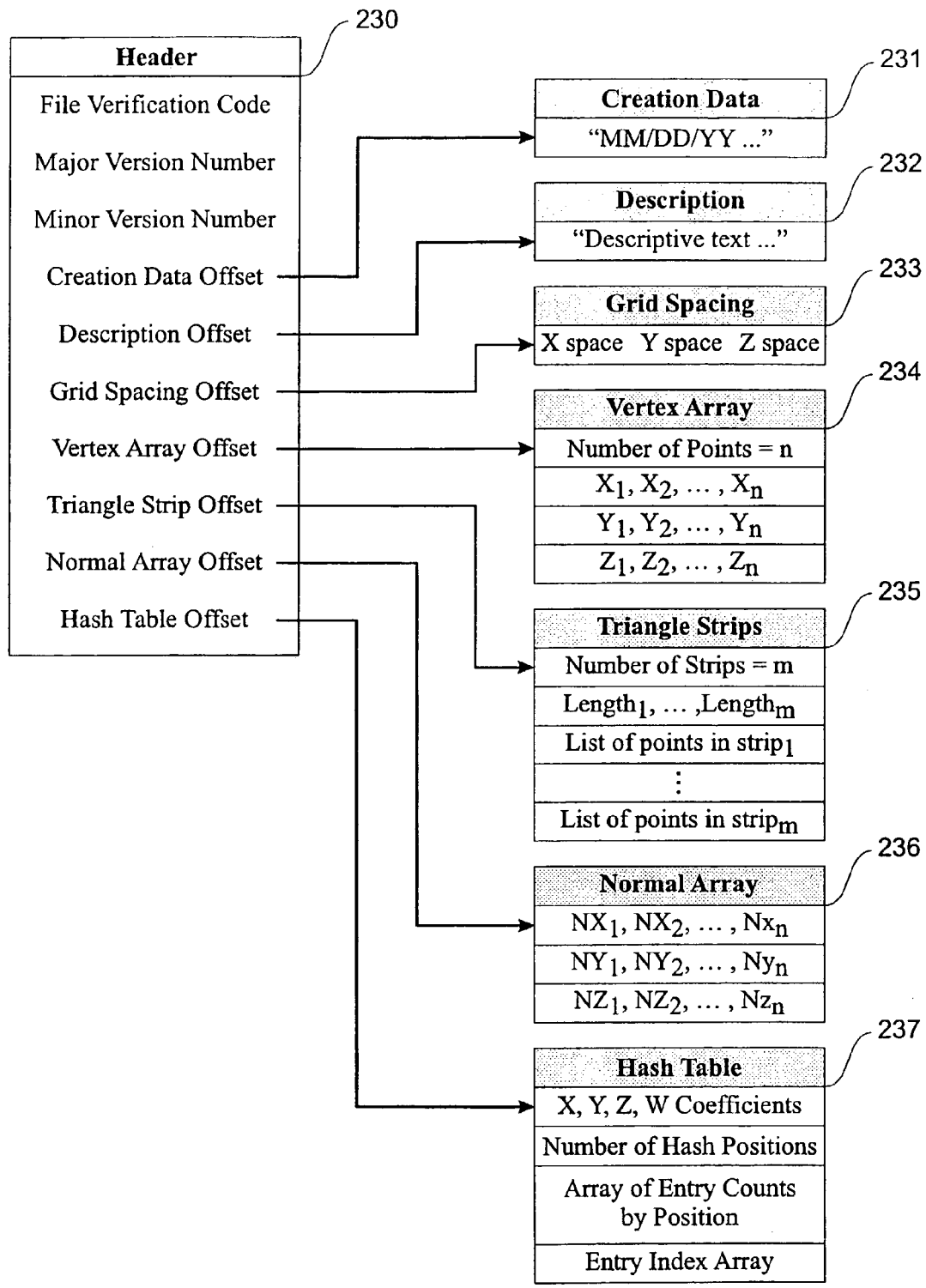
FIG. 17 is block diagram illustrating the file format specification for the Virtual Dental Patient Record Data Sets.

As illustrated in FIG. 1, the processed data is stored in the Data Storage Device 3 as a Record Data Set 10. The file format used in some embodiments of the Virtual Dental Patient Record Data Set is illustrated in a block form in FIG. 17. The Header file 230 contains information to verify which version of the software was used to create the data plus a list of offsets that define the location of different blocks of data. The Creation Data block 231 contains the date that the file was created. The Descriptive block 232 contains text describing the object that was scanned. The Grid Spacing block 233 defines the length of the sides of the rectangular volume grid. The Vertex Array block 234 contains the (x,y,z) coordinates of the averaged data points for the scanned record. The Triangle Strips block 235 contains the parameters defining the number of strips, the length of each strip, and a list of indices to the points in each strip. The Normal Array block 236 contains a second (x,y,z) coordinate that defines the normal vector for the corresponding point in the Vertex Array 234. The Hash Table 237 is used in some embodiments of the invention to organize the vertex data. However, in alternative embodiments of the invention, the Hash Table 237 is not used because it can be generated rapidly by a computer.

Figure 18:
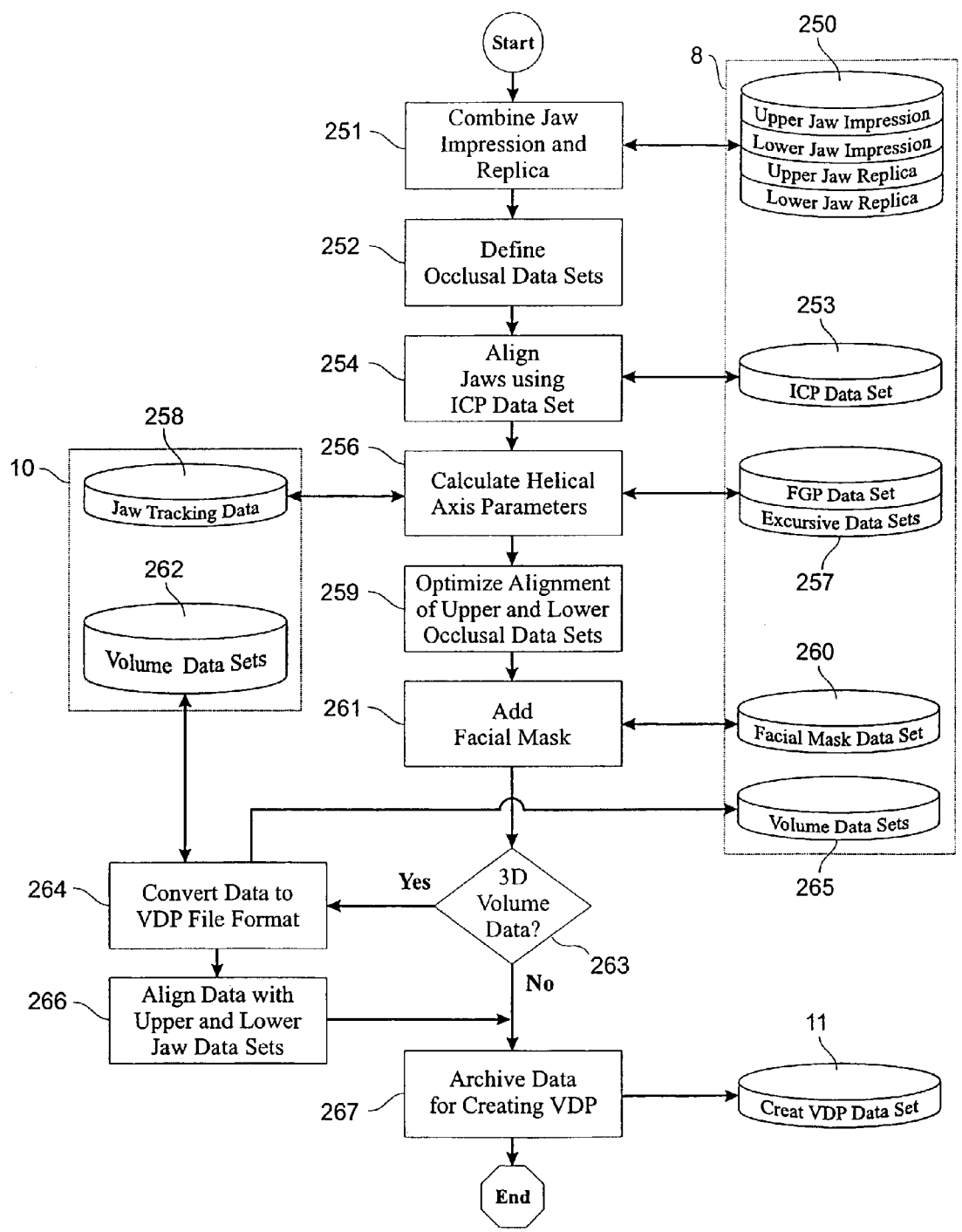
FIG. 18 is a block diagram illustrating the flow of the computer processes involved in the creation of the Virtual Dental Patient.

Computer processes used in some embodiments of the invention that are involved in the creation of the Virtual Dental Patient are illustrated in the block diagram of FIG. 18. Impression and replica data records 250 for each jaw, upper and lower, which are archived as Record Data Sets 8, are combined to produce a more complete jaw data set 250. In one embodiment, occlusal data is used to align the upper and lower jaw images and to determine the helical axis parameters; therefore, the data defining the occlusal portion is separated from the entire jaw database 252. Separating the occlusal data has the added benefit of simplifying the process and reducing computation time, however the present invention is not limited to separating the occlusal data. The ICP data set 253 is aligned with the jaw occlusal data sets using optimizing computer algorithms 254. Applying the resulting transformation matrix to the lower jaw data set aligns the jaw data sets. Helical axis parameters, which are used to control the motion of the lower jaw data set relative to the upper jaw data set, are calculated 256 from the FGP Data Set, the Excursive Data Sets, or the Jaw Tracking Data, or combinations of the three. The FGP and Excursive Data Sets 257 may be archived as Record Data Sets 8. The Jaw Tracking Data 258 may be archived as a Digital Data Set 10. Alignment of the upper and lower jaw data sets is refined 259 to account for the thickness of the ICP record and scanning errors. The lower jaw data set is rotated about the helical axes until optimal contact with the upper jaw data set is reached, which in one embodiment of the invention is determined by a contact algorithm. A three-dimensional facial mask data set 260, archived as a Data Record Set 8, is aligned 261 to the upper and lower jaw databases. The facial data set may be obtained from any scanner or camera capable of providing (x,y,z) coordinate points. The data representing the facial mask may be used to provide easy recognition of the patient and to provide a boundary for any three-dimensional volume data. Volume data sets 262, such as MRI, CT scans, etc., may be archived as Digital Data Sets 10. If Volume Data Sets are available 263, they may be converted to the VDP format 264 and archived as new Volume Data Sets 265 in the Data Record Set 8. The volume data is aligned with the jaw and facial data sets 266. In some embodiments, this completes the construction of the Virtual Dental Patient. The transformation and scaling matrices and the helical axis parameters required for the construction of the Virtual Dental Patient are archived as a Create Data Set 11. Details of the processes involved in the construction of the Virtual Dental Patient are described in greater detail below.

Combine Impression and Replica

Figure 19:
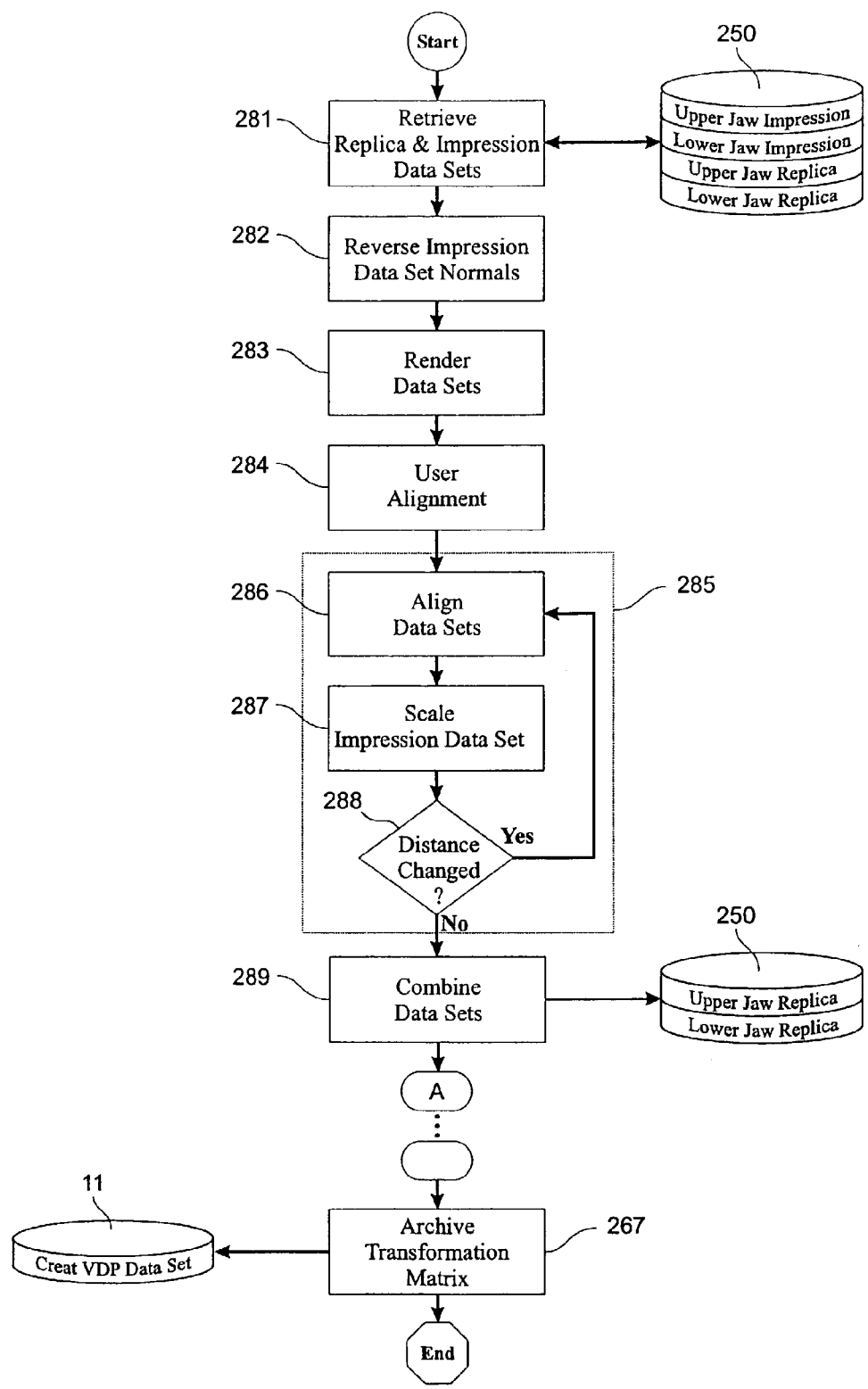
FIG. 19 is a flow diagram illustrating in greater detail the flow of the computer Processes used to align the replica and impression data sets.
Figure 20:
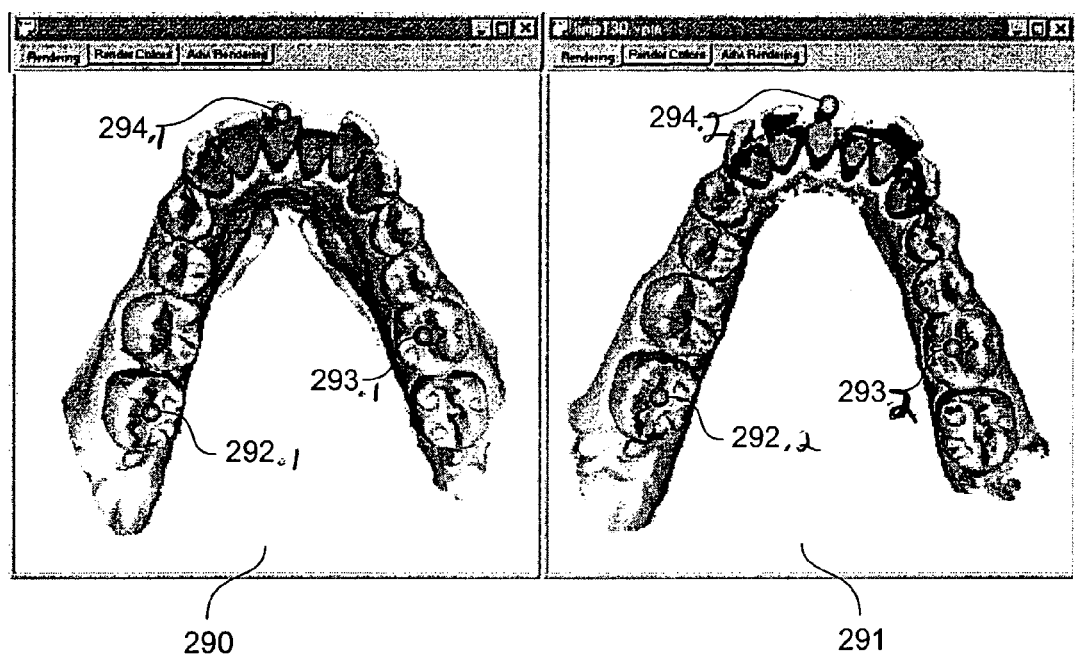
FIG. 20 is a bitmap image of the rendered replica and impression data sets for a lower jaw illustrating the points selected for the user alignment of the data sets.

FIG. 19 is a diagram illustrating the flow of the computer processes used in an embodiment of the invention to align the replica and impression data sets. It is desirable to combine the two data sets to improve the quality of the jaw images. Although this process is described in this embodiment of the invention, it is not required for the construction of the VDP. Archived data sets for the replica and impression are retrieved 281 from the Record Data Set 250. The normals for the impression data set are reversed 282 to make the back of the impression visible. This has the effect of creating a positive rendered image of the impression that is compared with the rendered image of the replica 283. Bitmap examples of the two rendered images, replica 290 and impression 291 are illustrated in FIG. 20. Because the optimization algorithms generally require that the two data sets be in close alignment, and because the impression data set and replica data sets can be created from different objects, the two data sets may first need to be aligned. In some embodiments, the data sets may be aligned manually through user input 284, however user alignment is not required in all embodiments. In these embodiments, the process requires the user to select three or more pairs of corresponding points, one point on each rendered image. FIG. 20 illustrates examples of selected points 292, 293, and 294. The alignment process generally minimizes the 3D distance between the corresponding pairs. Following the user alignment, the two data sets are aligned using a two-step optimizing process 285. The first step aligns the overlapping regions of the two data sets 286 as previously described in FIG. 7-FIG. 10. The second step scales the impression data set 287 to reduce the distance between the overlapping areas of the two data sets. Following the alignment process, the two data sets are combined to form a single data set 289, which can be archived as the Jaw Replica data set 250, replacing the original Jaw Replica data set. Combining the images follows a process similar to that described previously for combining the aligned scan data sets, process 76 (FIG. 6). The two steps are repeated until there is no change in the distance between the overlapping areas. The calculated transformation matrix may be archived 267 as one component of the Create Data Set 11.

Define Occlusal Data Sets

Figure 21:
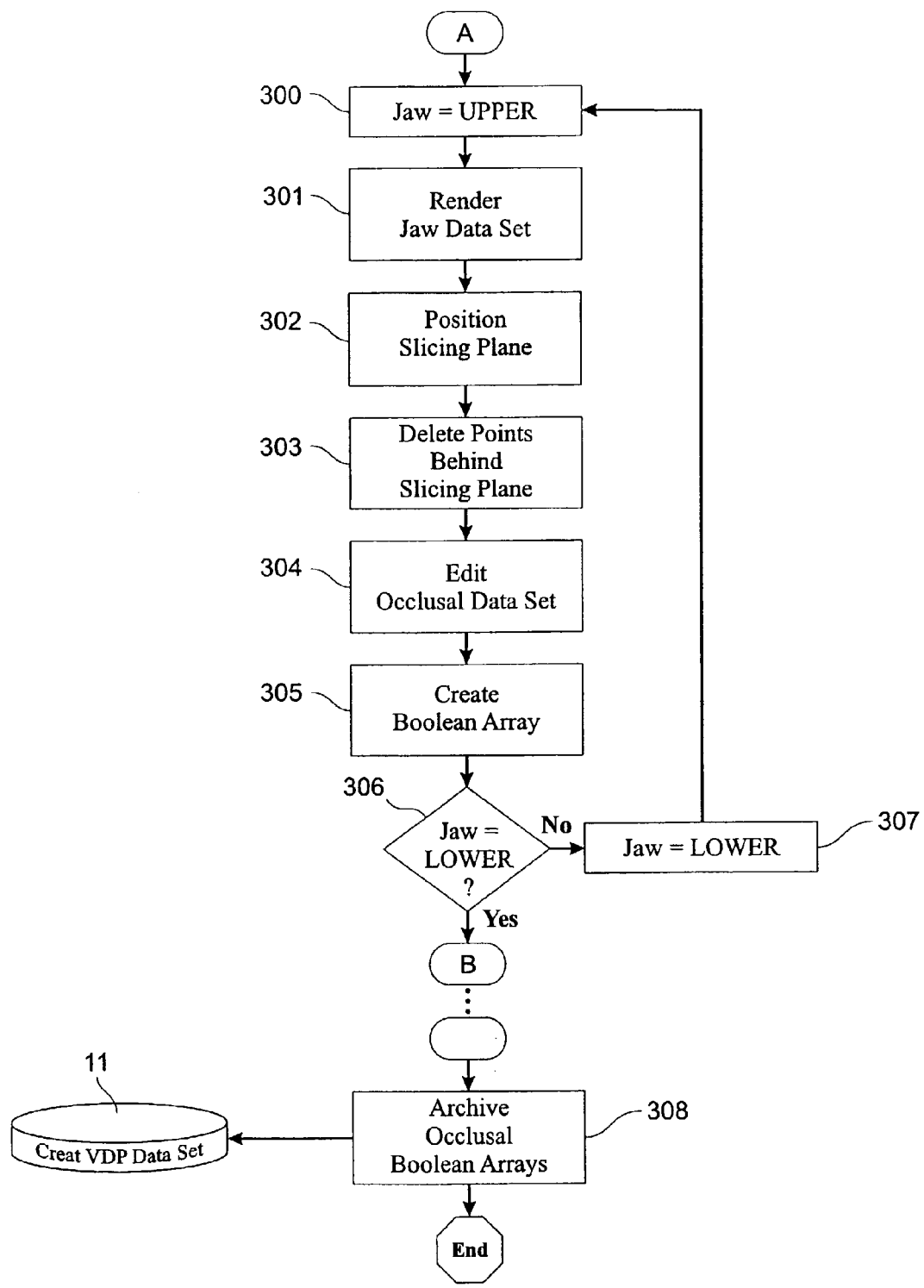
FIG. 21 is a flow diagram illustrating the flow of the computer processes used to create the occlusal data set.
Figure 22:
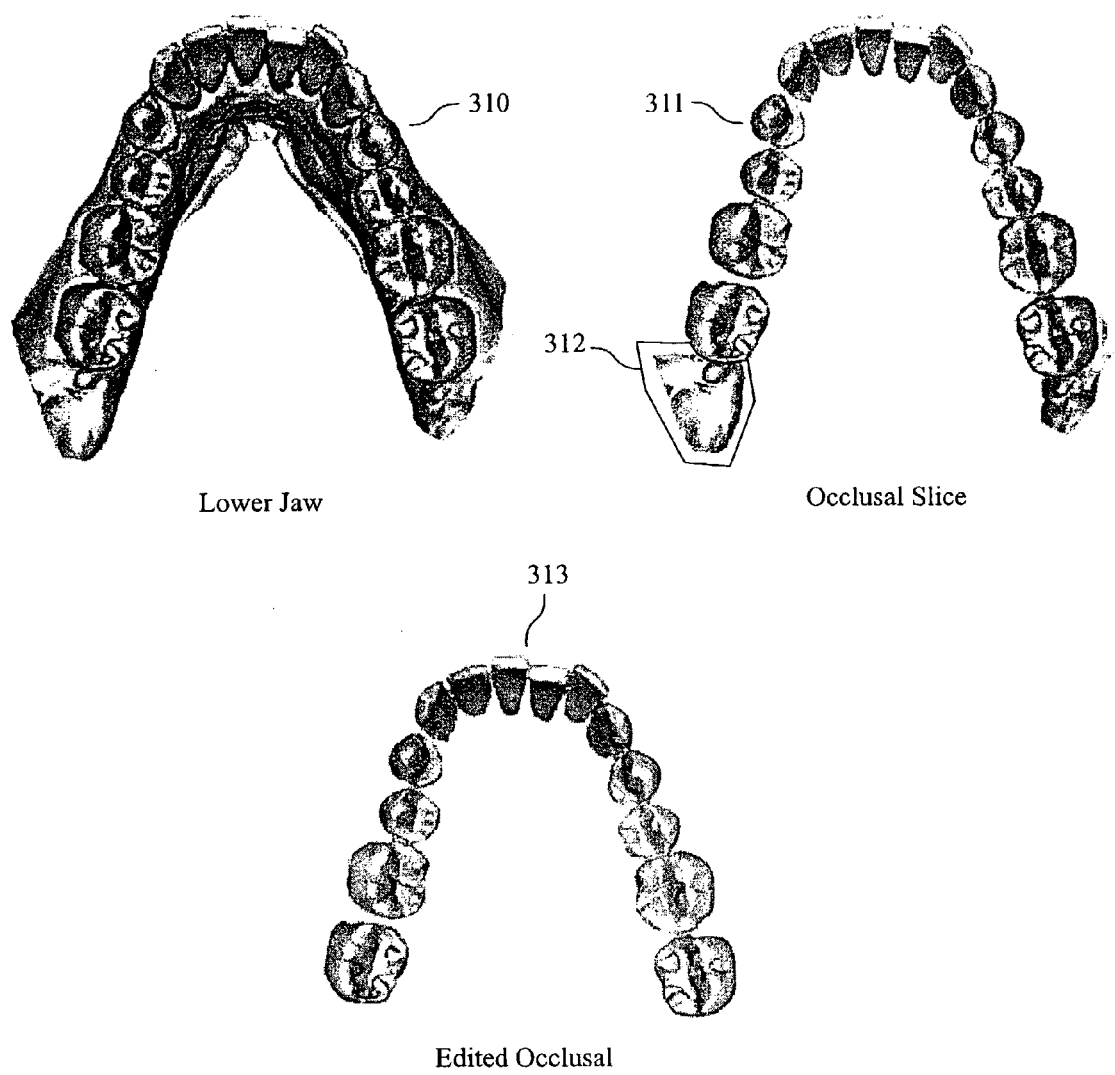
FIG. 22 is an illustration of the bitmapped images of the rendered lower jaw data set and the unedited and edited occlusal data sets.
Figure 23:
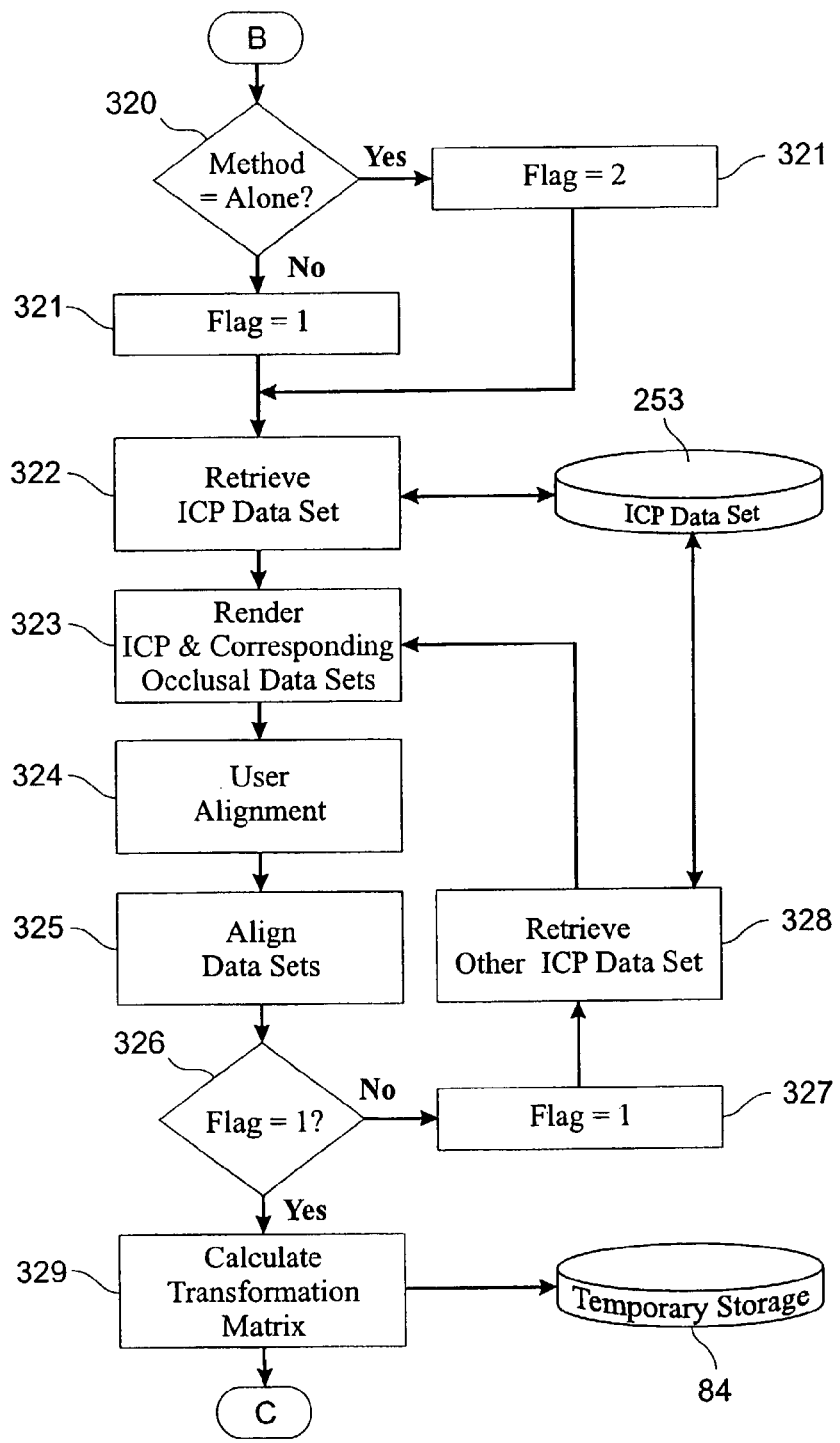
FIG. 23 is a flow diagram illustrating the computer processes that align the upper and lower jaw data sets using the ICP data set.

The flow of a method according to an embodiment of the invention that can be used to create the occlusal data sets is illustrated in FIG. 21. In some embodiments, the upper jaw data set is selected 300 and rendered 301 on the computer monitor. In one embodiment of the invention, the user manually positions 302 the plane that defines the occlusal portion of the data set; however, an alternative embodiment of this invention defines this plane using computer algorithms with no user input. The latter process will be described below. In one embodiment, all points in the jaw data set that lie above the plane are visible on the monitor and are tagged as belonging to the Occlusal Data Set. Not all of the points above the plane are necessarily part of the tooth anatomy. These points may be edited from the Occlusal Data Set 304 using a line tool to define the non-tooth regions. A boolean array is created 305 to tag the points in the Jaw Data Set that belong to the Occlusal Data Set. The process is repeated 306 for the Lower Jaw Data Set 307. The occlusal Boolean arrays for the upper and lower jaw data sets are archived 308 in the Create VDP Data Set 11. FIG. 22 illustrates exemplary bitmaps of the rendered lower jaw data set 310 and the unedited occlusal data set 311. The black line 312 defines a region that is to be edited out of the occlusal data set. The lower exemplary bitmap 313 is the rendition of the final Occlusal Data Set.

Fit Jaws Using ICP Record

The upper and lower data sets may be initially aligned using the ICP clinical record data set 253. The ICP record may be used in two different ways 320 to align the upper and lower data sets, including scanned seated on the replica or scanned alone. The first method typically involves only one alignment process, while the latter method typically involves two alignment processes. If the ICP record was scanned alone, then the two sides, upper and lower, of the ICP record may be stored as separate data sets. A Flag variable 321 defines which method was used. An ICP data set is retrieved 322 from the data storage device. The ICP record and the corresponding occlusal data set, the occlusal data set whose tooth indentations were recorded by the ICP record, are rendered on the computer monitor 323. In one embodiment, the user performs a preliminary alignment 324 of the two data sets by selecting at least three pairs of corresponding points as described in FIG. 20. The optimization procedure 325, which minimizes the distance between each point in the occlusal data set and its corresponding point in the ICP data set, is the same as that described in FIG. 7-FIG. 10. If the ICP record was scanned alone 326, a second alignment is involved that uses the other side of the ICP record and its corresponding occlusal data set.

Figure 24:
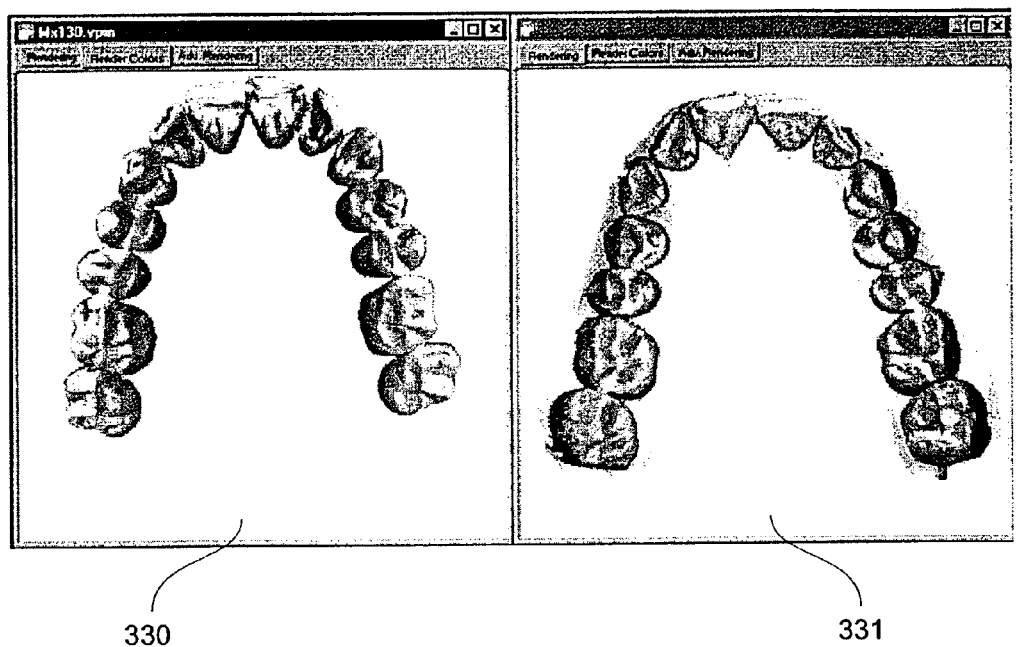
FIG. 24 is a bitmap illustration of the rendered upper occlusal data set and the upper side of the ICP data set.

In this case, the Flag variable is reset to a value indicating that a second alignment is to be done, for example a 1 (one) 327, and the other ICP data set is retrieved 328. A transformation matrix is calculated 329 from the matrices used to align the data sets, and may be stored temporarily in the temporary storage device 84. This transformation matrix, when applied to the lower jaw data set, aligns the lower jaw data set with the upper jaw data set. The two sets may not be in optimal alignment because the ICP record has a finite thickness. Correction for the thickness of the ICP record is described below. FIG. 24 is a bitmap illustration of an upper occlusal data set 330 and the upper ICP data set 331 rendered on the computer monitor.

Calculate Helical Axis Parameters

Helical axis parameters, which calculate motion as rotation about, and a translation along a helical axis, control movement of the lower jaw data set relative to the upper jaw data set. The position of the lower jaw data set is defined by the distance that a control point moves from the start position, which is defined to be ICP. The helical axis parameters are calculated using a set of target points selected from points in the lower jaw data set. In one embodiment, positioning the lower jaw data set at two distinct locations and knowing the positions of the target points at these two positions provides the data used to calculate the helical axis parameters. The various embodiments of the invention include any one or more of at least four different methods for calculating the helical axis parameters: average values, based on excursive records, based on a FGP, and based on jaw tracking data.

Figure 25:
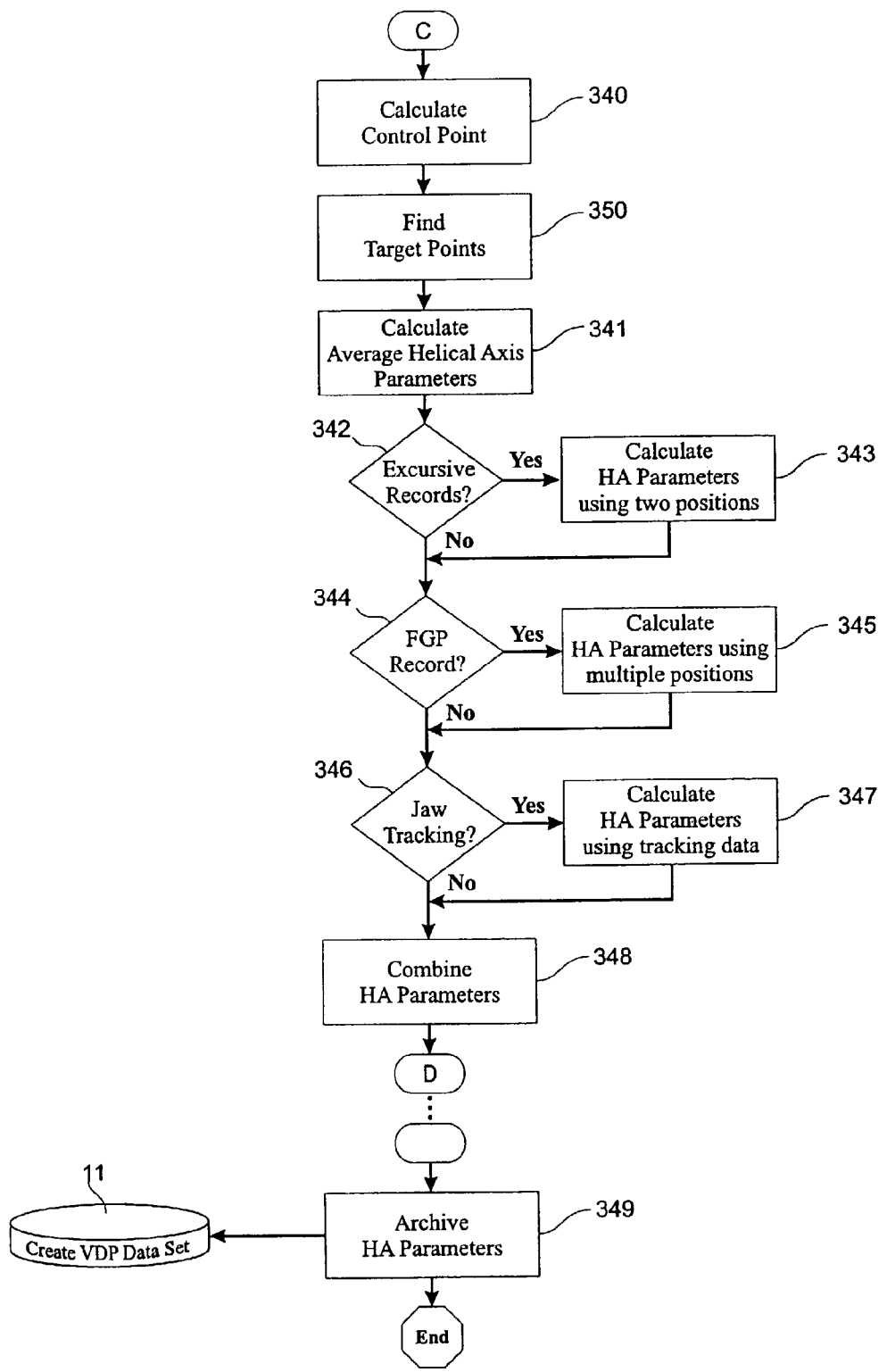
FIG. 25 is a diagram illustrating the flow of the computer routines used to calculate the helical axis (HA) parameters.

The flow of the computer routines used to calculate the helical axis parameters according to the various embodiments is illustrated in FIG. 25. The location of a control point, u, is calculated for the lower jaw data set 340. A set of target points is selected from the lower jaw data set 350. The control point is one point in this set. Based on the dimensions of the jaw data sets and clinically measured values for maximum right and left jaw movement, maximum opening, and maximum protrusion of the lower jaw relative to the upper jaw, the helical axis parameters are calculated as a function of u 341. If excursive data sets exist 342, then a set of helical axis parameters are calculated using these data sets 343. The excursive data sets provide a second position of the lower jaw data set relative to the upper jaw data set that is used to calculate the parameters. This process is described in more detail below.

If a FGP data set exists 344, then the helical axis parameters may be calculated using this data set 345. The FGP provides multiple positions of the lower jaw relative to the upper jaw. This process is described in more detail below.

If jaw-tracking data exists 346, then this data may be used to calculate the helical axis parameters 347. Jaw tracking is typically the only data that provides information about the lower jaw movement when the teeth are not in contact.

Figure 27:
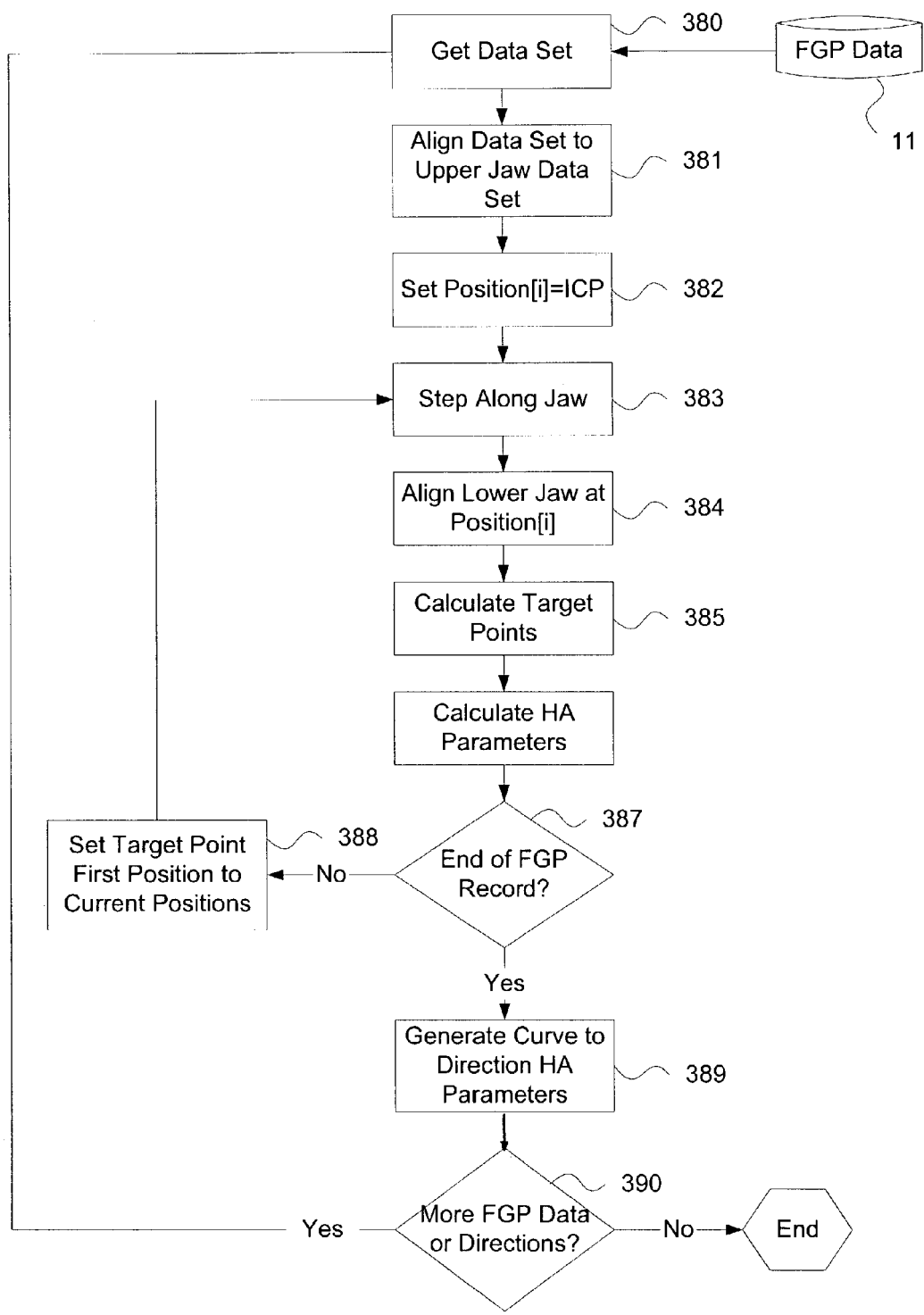
FIG. 27 is a diagram illustrating the flow of the computer routines used to calculate the helical axis parameters using a FGP.
Figure 28:
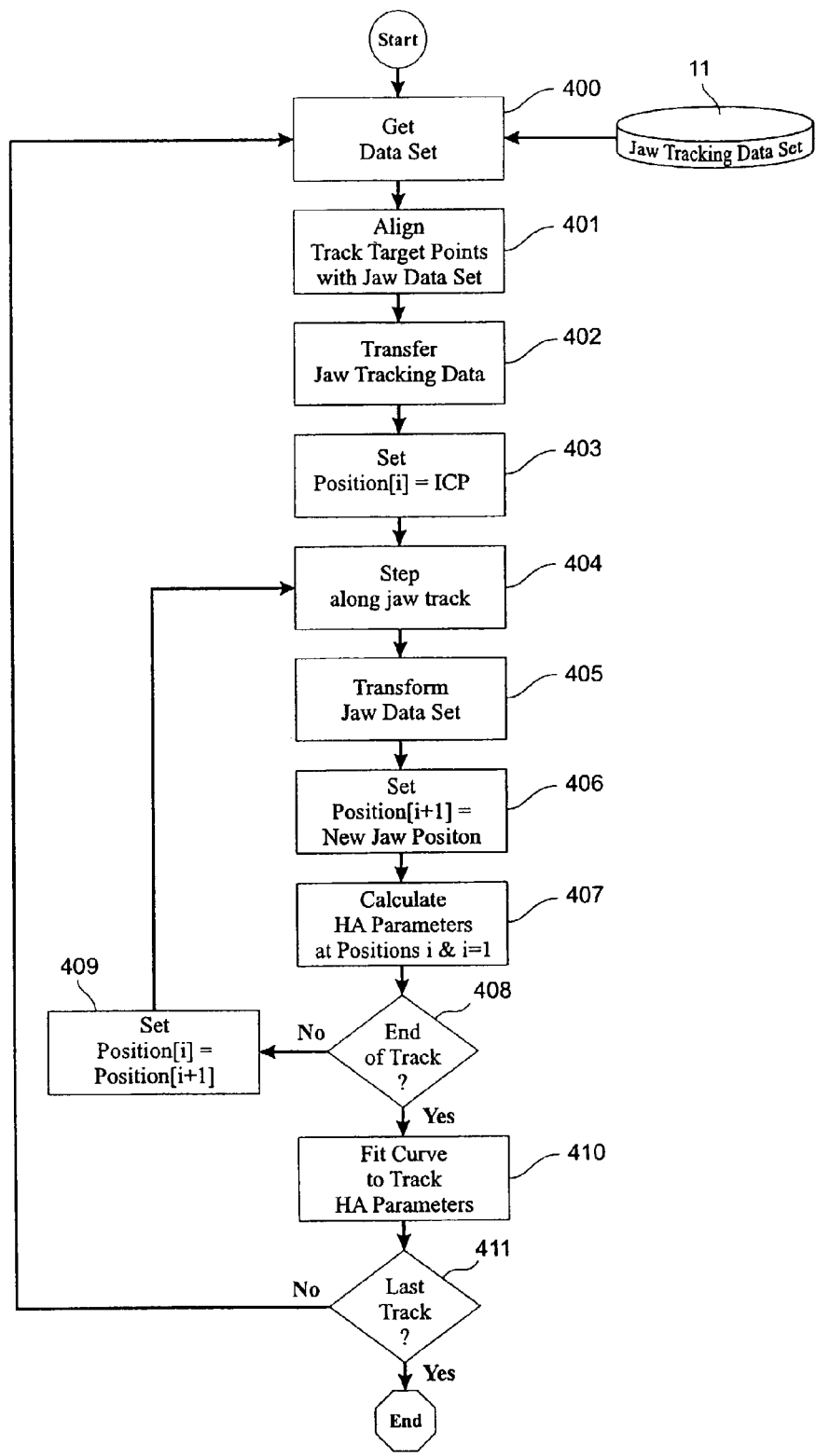
FIG. 28 is a diagram illustrating the flow of the computer routines used to calculate the helical axis parameters using jaw tracking data.

In the various embodiments, all helical parameters, regardless of the method used, are calculated as a function of the control parameter u. The available calculated parameters are combined to create a final set of helical axis parameters 348. Not all methods are required. Where information is missing, the average helical axis parameters are used. The final set of helical axis parameters is archived as part of the Create VDP Data Set 349. The processes for calculating the helical axis parameters using the different clinical records is illustrated in FIGS. 26-28 and described in greater detail below.

Calculation of Helical Axis Parameters Using Excursive Records

Figure 26:
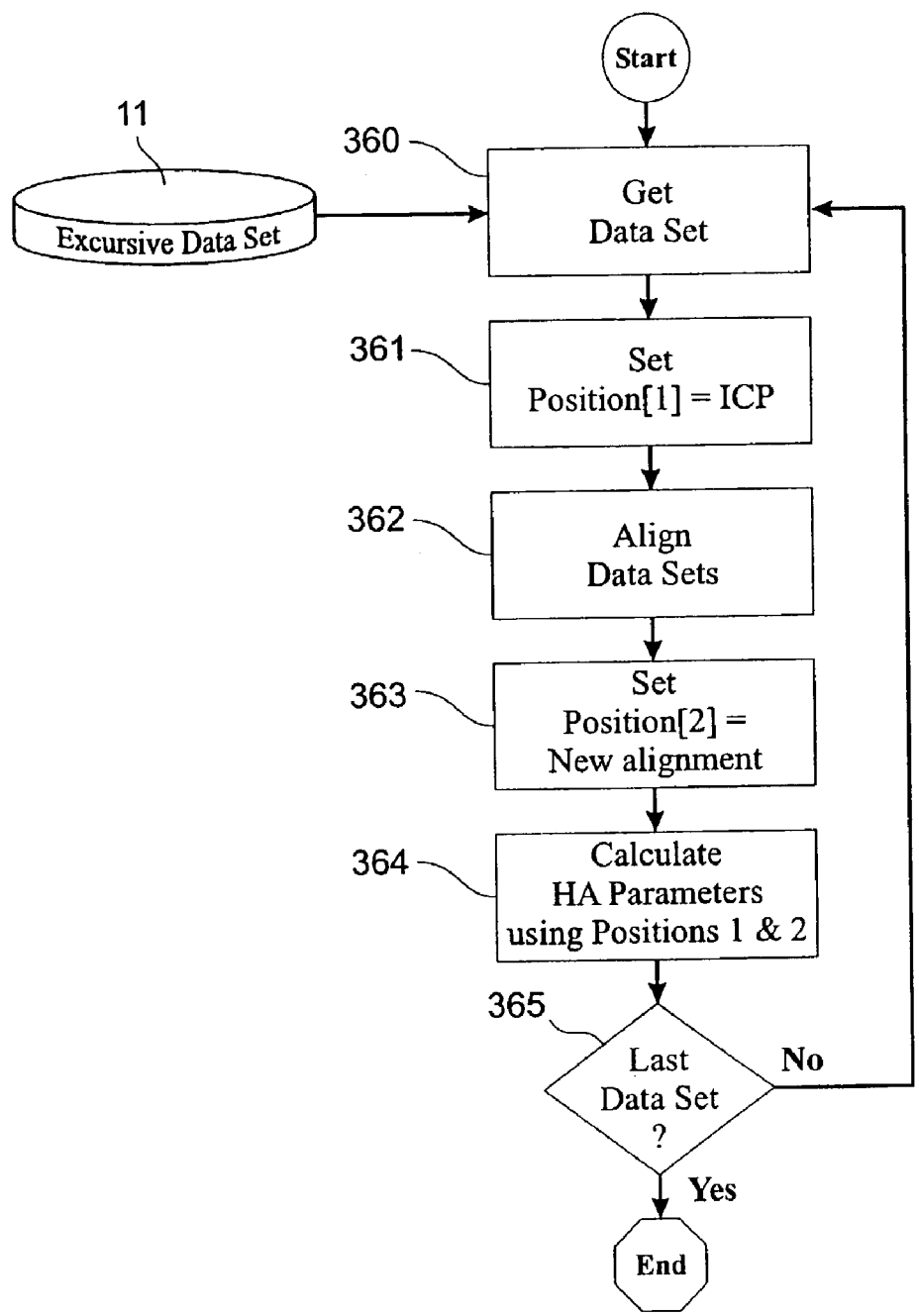
FIG. 26 illustrates the flow of the computer routines used to calculate the helical axis parameters from two positions of the lower jaw data set.

FIG. 26 illustrates the flow of the computer routines used in various embodiments of the invention for calculating the helical axis parameters from a second position of the lower jaw relative to the upper jaw. Calculation of the helical axis parameters uses the location of the target points at two distinct positions. The first position is the ICP alignment of the lower jaw data set with the upper jaw data set. A second position is determined using excursive records. These records are identical to the ICP record except that the jaw is located at another position. In one embodiment, the Excursive Data Set contains up to four different data sets: one with the jaw positioned to the right, one with the jaw positioned to the left, one with the jaw positioned forward, and one with the jaw opened. Each data set has a distinct set of helical axis parameters. Not all data sets are required, and there could be more than one data set for each direction of movement. One Excursive Data Set is retrieved 360 from the storage device 11. The location of the target points for the first position, which is the ICP position, is stored temporarily 361. The lower data set is aligned 362 to the upper data set following the same method used to align the two data sets at the ICP position. The location of the target points is calculated for the new position 363. Using the two locations for the target points, the helical axis parameters are calculated and stored temporarily 364. If there is a second Excursive Data Set the process is repeated 365 for this set. The process continues until the helical axis parameters have been calculated for all of the available Excursive Data Sets.

Calculation of Helical Axis Parameters Using FGP Records

FIG. 27 illustrates the flow of the computer routines used in some embodiments of the invention to calculate the helical axis parameters from a FGP. The FGP records the motion of the lower jaw as it moves to the right, left, or forward relative to the upper jaw. The motions may be recorded on a single record that records all three directions or on multiple records that record only one direction. It typically only records motion while the teeth are in contact. A FGP data set is retrieved 380 from the data storage device 11. The data set is aligned 381 to the upper jaw data set following the same process used to align the ICP data set to the upper jaw data set. The first position of the jaw is set to the ICP position 382. Locations of the target points at this position are stored temporarily. Multiple positions of the lower jaw data set are calculated using the FGP by stepping the lower jaw along the FGP data set in a specified direction 383 then aligning the lower jaw data set to the FGP at this position 384. After the step is made the step parameter is fixed for the alignment. For example, if the step is in the "x" direction, then the lower jaw data set cannot move along the X-axis during the alignment process. All other parameters can change freely. The FGP alignment process is a variation of the process used to align the ICP data set to the upper occlusal data set. One variation is that there is one less variable parameter: the step direction. A second variation is that the two data sets generally cannot pass through each other. These changes are desirable because the two surfaces represented by the data sets are typically not identical, as was the case for the ICP and upper occlusal data set. After the optimized alignment is reached, the locations of the target points are calculated 385 followed by the calculation of the helical axis parameters for this step 386. A test is made to see if the lower jaw data set is at the end of the FGP record 387. If it is not, the first positions of the target points are set equal to the current positions of the target points 388. The jaw data set is stepped in the same direction to the next location and the process is repeated. When the end of the FGP is reached for the selected direction, in one embodiment, a smooth curve is generated through each of the helical axis parameter sets for the selected direction 389. This has the effect of smoothing processing errors and provides continuous equations for the parameters as a function of the location of the control point. The process is repeated for all available FGP data sets or directions 390 for the selected patient. Normally, there will be three sets of equations for each of the helical axis parameters: right, left, and forward.

Calculation of Helical Axis Parameters Using Jaw Tracking Data

FIG. 28 illustrates the flow of the computer routines used in one embodiment of the invention for calculating the helical axis parameters using jaw tracking data. Jaw tracking generally provides information about the movement of the lower jaw relative to the upper jaw both when the teeth are in contact and when they are out of contact. The data consists of the paths of motion for at least three non-collinear orientation points on the lower jaw. The coordinates of these three points as they move along the path of motion and the descriptions of the anatomical locations of the three points may be archived in the Jaw Tracking Data Set. The tracking data is retrieved 400 from the data storage device 11. The orientation points may be rendered as a rigid body that may be moved independently relative to the rendered image of the lower jaw data set. In some embodiments, the points are manually aligned 401 to the rendered image of the lower jaw data set using the anatomical descriptions. The resulting transformation matrix is used to transform the tracking data to the lower jaw data set coordinate system 402. The first position of the path is used to calculate the location of the target points 403. Normally, the first position is ICP; however, this is not a requirement. The next location of the orientation points in the jaw tracking data is found 404 and the lower jaw data set is transformed to this position 405. The target point coordinates are calculated for this position 406 followed by the calculation of the helical axis parameters 407. If the end of the track has not been reached 408, the first location of the target points is set equal to the current location of the target points and the process is repeated for a next location of the orientation points. In one embodiment, at the end of the track, a smooth curve is fit through the step data for each of the helical axis parameters 410 for the selected track. The process is repeated 411 for all of the tracking data sets available for the patient.

The virtual dental patient data in population database 18 can be used in a variety of methods. An individual VDP data set 5 can be sent to a CAD/CAM (Computer Aided Design/Computer Aided Manufacturing) systems or other rapid prototyping systems, where the data can be used to reproduce models of the tissues, or for the reproduction of prosthetic equipment for the tissues.

In addition, VDP data sets can be compared against one another in order to determine changes in a patient's condition over time. For example, a VDP data set 5 acquired at a first point in time can be compared with a VDP data set 5 acquired at a second point in time. The comparison can be a statistical comparison, or the comparison can be a graphical comparison involving the superimposition of the data. In addition, the fitting algorithms described above can be used to fit the two data sets together to insure that the data is superimposed correctly. Changes in tooth movement, hard tissue erosion and changes in the soft tissues can be noted. In addition, changes in the position of a helical axis can be determined and analyzed.

For example, as noted above, statistical analysis 16 can be performed across all of the VDP data sets in the population database 18. The statistical analysis can be used to establish norms based on age, sex, and/or ethnic backgrounds. Individual VDP data sets can then be compared against the norms, and any deviations can be reported on, or displayed graphically.

In addition, the VDP data sets can be added to a facial mask. For example, a patient's face may be scanned twice, once with a smile thereby exposing the patient's teeth, and once without a smile. The VDP data sets can then be fitted to the face by aligning the VDP data set to the teeth in the image with a smile.

Additionally, the VDP data set may be used to predict tooth movement under function. Fore example, the computer generated contacts in the VDP data sets may be compared to clinically recorded contacts, and the difference used to predict tooth movement.

This section has described the various software components in a system that create and maintain data sets for virtual dental patients. As those of skill in the art will appreciate, the software can be written in any of a number of programming languages known in the art, including but not limited to C/C++, Java, Visual Basic, Smalltalk, Pascal, Ada and similar programming languages. The present invention is not limited to any particular programming language for implementation.

Hardware Operating Environment

Figure 29:
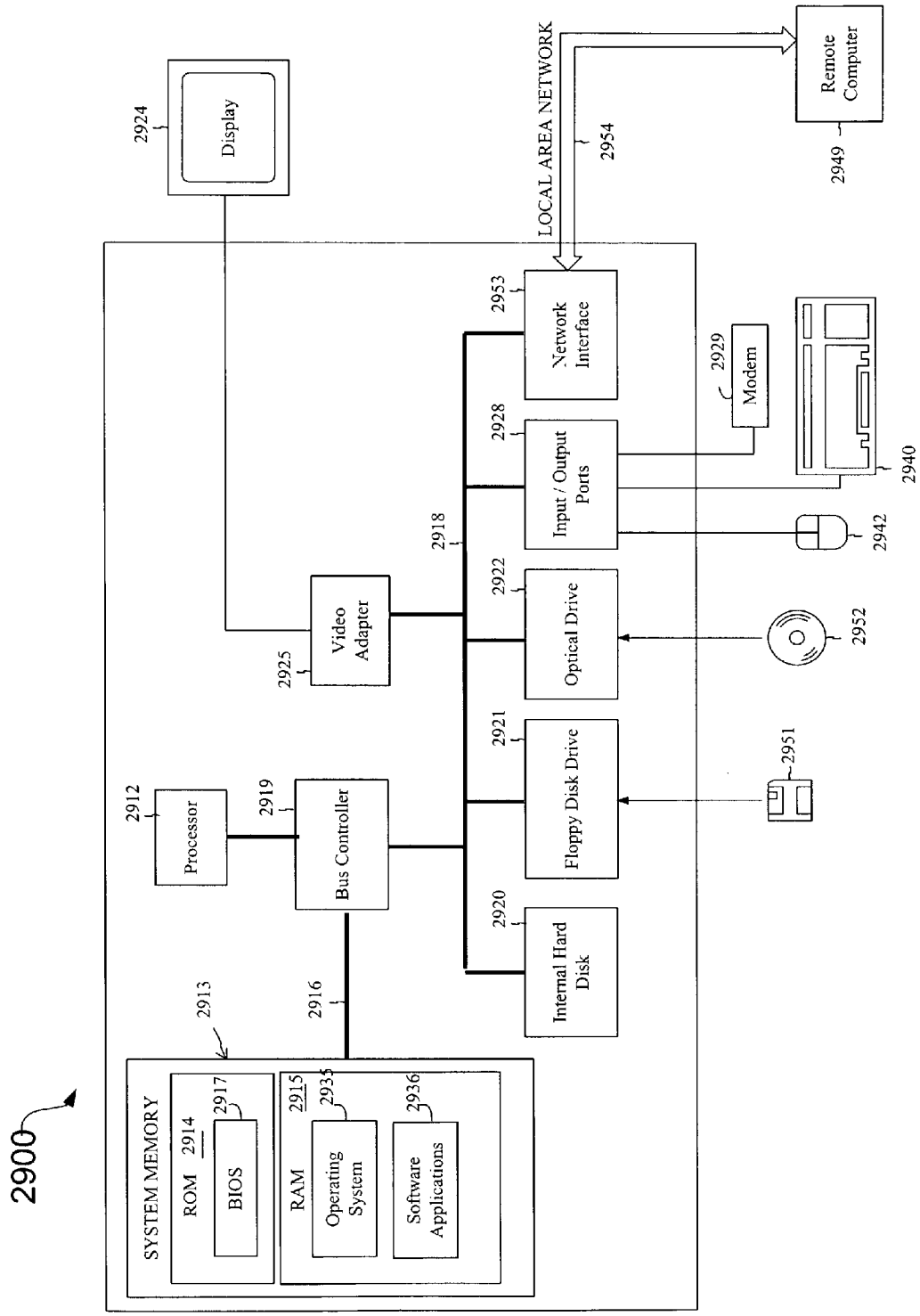
FIG. 29 is a diagram illustrating an exemplary hardware and software environment on which embodiments of the invention may be executed.

FIG. 29 is a diagram of the hardware and operating environment in conjunction with which embodiments of the invention may be practiced. The description of FIG. 29 is intended to provide a brief, general description of suitable computer hardware and a suitable computing environment in conjunction with which embodiments of the invention may be implemented. Although not required, the present invention is described in the general context of computer-executable instructions, such as program modules, being executed by a computer, such as a personal computer or a server computer. Generally, program modules include routines, programs, objects, components, data structures, etc., that perform particular tasks or implement particular abstract data types.

Moreover, those skilled in the art will appreciate that the present invention may be practiced with other computer system configurations, including hand-held devices, multiprocessor systems, microprocessor-based or programmable consumer electronics, network PCs, minicomputers, mainframe computers, and the like. The present invention may also be practiced in distributed computing environments where tasks are performed by remote processing devices that are linked through a communications network. In a distributed computing environment, program modules may be located in both local and remote memory storage devices.

As shown in FIG. 29, the computing system 2900 includes a processor. The present invention can be implemented on computers based upon microprocessors such as the PENTIUM® family of microprocessors manufactured by the Intel Corporation, the MIPS® family of microprocessors from the Silicon Graphics Corporation, the POWERPC® family of microprocessors from both the Motorola Corporation and the IBM Corporation, the PRECISION ARCHITECTURE® family of microprocessors from the Hewlett-Packard Company, the SPARC® family of microprocessors from the Sun Microsystems Corporation, or the ALPHA® family of microprocessors from the Compaq Computer Corporation. Computing system 2900 represents any personal computer, laptop, server, or even a battery-powered, pocket-sized, mobile computer known as a hand-held PC.

The computing system 2900 includes system memory 2913 (including read-only memory (ROM) 2914 and random access memory (RAM) 2915), which is connected to the processor 2912 by a system data/address bus 2916. ROM 2914 represents any device that is primarily read-only including electrically erasable programmable read-only memory (EEPROM), flash memory, etc. RAM 2915 represents any random access memory such as Synchronous Dynamic Random Access Memory.

Within the computing system 2900, input/output bus 2918 is connected to the data/address bus 2916 via bus controller 2919. In one embodiment, input/output bus 2918 is implemented as a standard Peripheral Component Interconnect (PCI) bus. The bus controller 2919 examines all signals from the processor 2912 to route the signals to the appropriate bus. Signals between the processor 2912 and the system memory 2913 are merely passed through the bus controller 2919. However, signals from the processor 2912 intended for devices other than system memory 2913 are routed onto the input/output bus 2918.

Various devices are connected to the input/output bus 2918 including hard disk drive 2920, floppy drive 2921 that is used to read floppy disk 2951, and optical drive 2922, such as a CD-ROM drive that is used to read an optical disk 2952. The video display 2924 or other kind of display device is connected to the input/output bus 2918 via a video adapter 2925.

A user enters commands and information into the computing system 2900 by using a keyboard 2940 and/or pointing device, such as a mouse 2942, which are connected to bus 2918 via input/output ports 2928. Other types of pointing devices (not shown in FIG. 29) include track pads, track balls, joy sticks, data gloves, head trackers, and other devices suitable for positioning a cursor on the video display 2924.

As shown in FIG. 29, the computing system 2900 also includes a modem 2929. Although illustrated in FIG. 29 as external to the computing system 2900, those of ordinary skill in the art will quickly recognize that the modem 2929 may also be internal to the computing system 2900. The modem 2929 is typically used to communicate over wide area networks (not shown), such as the global Internet. The computing system may also contain a network interface card 2953, as is known in the art, for communication over a network 2954.

Software applications 2936 and data are typically stored via one of the memory storage devices, which may include the hard disk 2920, floppy disk 2951, CD-ROM 2952 and are copied to RAM 2915 for execution. In one embodiment, however, software applications 2936 are stored in ROM 2914 and are copied to RAM 2915 for execution or are executed directly from ROM 2914.

In general, the operating system 2935 executes software applications 2936 and carries out instructions issued by the user. For example, when the user wants to load a software application 2936, the operating system 2935 interprets the instruction and causes the processor 2912 to load software application 2936 into RAM 2915 from either the hard disk 2920 or the optical disk 2952. Once software application 2936 is loaded into the RAM 2915, it can be used by the processor 2912. In case of large software applications 2936, processor 2912 loads various portions of program modules into RAM 2915 as needed.

The Basic Input/Output System (BIOS) 2917 for the computing system 2900 is stored in ROM 2914 and is loaded into RAM 2915 upon booting. Those skilled in the art will recognize that the BIOS 2917 is a set of basic executable routines that have conventionally helped to transfer information between the computing resources within the computing system 2900. These low-level service routines are used by operating system 2935 or other software applications 2936.

In one embodiment computing system 2900 includes a registry (not shown) which is a system database that holds configuration information for computing system 2900. For example, Windows® 95, Windows 98®, Windows® NT, and Windows 2000® by Microsoft maintain the registry in two hidden files, called USER.DAT and SYSTEM.DAT, located on a permanent storage device such as an internal disk.

CONCLUSION

Systems and methods for creating and maintaining a virtual dental patient are disclosed. The various embodiments of the invention provide advantages over previous systems. For example, the use of clinical records in creating the virtual dental patient provides for more accurate representation of the images representing the patient than in previous systems. Moreover, the inclusion of jaw movement records provides the ability to accurately model the movement of the jaw within the virtual dental patient, thereby allowing accurate functional examination of the VDP. The examination of the VDP can allow determinations and diagnoses to be made that are equal to those made on actual patients, without the potential pain and inconvenience to the patient.

The VDP of the various embodiments of the invention may be used in various ways, including but not limited to:

- Study and prediction of growth and development by providing numerical comparison of sequential images.
- Simulation of orthodontic movement by importing force, movement and property parameters of tissues and materials.
- Monitoring changes in soft and hard tissue morphology and texture.
- Clinical self-instruction and supervised instruction of students to advance their knowledge and skills before, during and after patient treatment.
- Use by examining bodies as a partial or full surrogate for clinical examination thereby relieving the medico-legal burden of treating patients with unqualified students.
- Data transmission of patient details to consultants, colleagues for review, feedback, and/or permission for treatment. Different remote users can access the VDP at the same time, thereby enabling true data-conferencing.
- The VDP can be connected to a rapid prototyper, mill or other device to produce replicas of body parts or prosthetic replacements for body parts.

Although specific embodiments have been illustrated and described herein, it will be appreciated by those of ordinary skill in the art that any arrangement which is calculated to achieve the same purpose may be substituted for the specific embodiments shown. This application is intended to cover any adaptations or variations of the present invention.

The terminology used in this application is meant to include all of these environments. It is to be understood that the above description is intended to be illustrative, and not restrictive. Many other embodiments will be apparent to those of skill in the art upon reviewing the above description. Therefore, it is manifestly intended that this invention be limited only by the following claims and equivalents thereof.

We claim:

1. A computerized method of representing a virtual dental patient, the method comprising:
   receiving a set of clinical records of a patient;
   receiving at least one jaw movement record; and
   determining by one or more processors at least one helical axis using the set of clinical records and the at least one jaw movement record, wherein the at least one helical axis is determined in accordance with at least a first jaw position and a second jaw position in the at least one jaw movement record, and further wherein the at least one helical axis controls the motions of a lower jaw data set relative to an upper jaw set;
   wherein the at least one jaw movement record comprises a functionally generated path (FGP), said FGP representing a plurality of lower jaw positions and wherein determining at least one helical axis comprises:
      determining a control point in a set of target points on the FGP, the control point and the target points comprising points in the lower jaw data set;
      aligning a first position of the FGP to an upper jaw data set;
      determining a first location for the set of target points on the first position of the FGP;
      selecting a step direction; and
      for each of a subset of the plurality of positions in the FGP performing the tasks of:
         determining a next position by stepping along the FGP in the step direction;
         aligning the new position to the FGP,
         determining a next location for the set of target points, and
         determining a helical axis parameter set from the first location and the next location, the helical axis parameter set including at least one parameter determined as a function of the control point.

2. The method of claim 1, wherein the set of clinical records includes at least one scanned analog record.

3. The method of claim 2, wherein the at least one scanned analog record is selected from the set consisting of: an upper jaw impression, a lower jaw impression, and a bit registration record.

4. The method of claim 1, wherein the set of clinical records includes at least one digital record.

5. The method of claim 4, wherein the at least one digital record is selected from the set consisting of: three dimensional facial images, MRI (Magnetic Resonance Imaging) scans, CT (Computer Tomography) scans.

6. The method of claim 1, wherein the jaw movement record comprises jaw tracking data.

7. The method of claim 1, further comprising fitting a first record of the set of clinical records to a second record of the set of clinical records.

8. The method of claim 1, further comprising rendering a three-dimensional image based on the clinical data records and the helical axis.

9. A computerized method of representing a virtual dental patient, the method comprising:
   receiving a set of clinical records of a patient;
   receiving at least one jaw movement record: and
   determining by one or more processors at least one helical axis using the set of clinical records and the at least one jaw movement record, wherein the at least one helical axis is determined in accordance with at least a first jaw position and a second jaw position in the at least one jaw movement record and further wherein the at least one helical axis controls the motions of a lower jaw data set relative to an upper jaw set;
   wherein determining at least one helical axis further comprises:
      determining a control point in a set of target points in the jaw movement record, the control point and the target points comprising points in the lower jaw data set;
      determining a location for the set of target points on a first jaw record representing a first position;
      aligning a second jaw record representing a second position;
      calculating a second location for the target points on the second jaw record;

determining the at least one helical axis from the first location and the second location, the helical axis comprising at least one parameter determined as a function of the control point.

10. The method of claim 9, wherein the jaw movement record comprises an excursive record.

11. A computerized system for representing a virtual dental patient, the system comprising:
a computer operable to:
receive a set of clinical records of a patient;
receive at least one jaw movement record;
determine a set of target points in the jaw movement record, the target points comprising points in a lower jaw data set;
determine a control point in the set of target points, the control point comprising a point in the lower jaw data; and
determine at least one helical axis using the set of clinical records and the at least one jaw movement record, the at least one helical axis including at least one parameter determined as a function of the control point; wherein the at least one helical axis is determined in accordance with at least a first jaw position and a second jaw position in the at least one jaw movement record, and further wherein the at least one helical axis controls the motions of a lower jaw data set relative to an upper jaw set; and
a data storage device communicably coupled to the computer and operable to store the set of clinical records, the at least one jaw movement record and the at least one helical axis.

12. The computerized system of claim 11, further comprising a surface scanner communicably coupled to the computer and for creating a scanned analog record, wherein the at least one helical axis is determined using the scanned analog record.

13. The computerized system of claim 11, further comprising a jaw tracking system communicably coupled to the computer and for creating the at least one jaw movement record.

14. The computerized system of claim 11, wherein the at least one jaw movement record is a functionally generated path.

15. The computerized system of claim 11, further comprising:
a volume scanner communicably coupled to the computer and operative to create digital clinical records; and
wherein the computer is further operable to insert the digital clinical records into the set of clinical records of the patient.

16. A computer-readable storage device having stored thereon computer executable instructions for performing a method of representing a virtual dental patient, the method comprising:
receiving a set of clinical records of a patient;
receiving at least one jaw movement record; and
determining at least one helical axis using the set of clinical records and the at least one jaw movement record, wherein the at least one helical axis is determined in accordance with at least a first jaw position and a second jaw position in each of at least two jaw movement records, and further wherein the at least one helical axis controls the motions of a lower jaw data set relative to an upper jaw set;
wherein the at least one jaw movement record comprises a functionally generated path (FGP), said FGP representing a plurality of lower jaw positions and wherein determining at least one helical axis comprises:
determining a control point in a set of target points on the FGP, the control point and the target points comprising points in the lower jaw data set;
aligning a first position of the FGP to an upper jaw data set;
determining a first location for a set of target points on the first position of the FGP;
selecting a step direction; and
for each of a subset of the plurality of positions in the FGP performing the tasks of:
determining a next position by stepping along the FGP in the step direction,
aligning the new position to the FGP,
determining a next location for the set of target points, and
determining a helical axis parameter set from the first location and the next location, the helical axis parameter set including at least one parameter determined as a function of the control point.

17. The computer-readable storage device of claim 16, wherein the set of clinical records includes at least one scanned analog record.

18. The computer-readable storage device of claim 17, wherein the at least one scanned analog record is selected from the set consisting of: an upper jaw impression, a lower jaw impression, and a bit registration record.

19. The computer-readable storage device of claim 16, wherein the set of clinical records includes at least one digital record.

20. The computer-readable storage device of claim 19, wherein the at least one digital record is selected from the set consisting of: three dimensional facial images, MRI (Magnetic Resonance Imaging) scans, CT (Computer Tomography) scans.

21. The computer-readable storage device of claim 16, wherein the jaw movement record comprises jaw tracking data.

22. The computer-readable storage device of claim 16, wherein the method further comprises rendering a three-dimensional image based on the clinical data records and the helical axis.

23. The computer-readable storage device of claim 16, wherein the method further comprises fitting a first record of the set of clinical records to a second record of the set of clinical records.

24. A computer-readable storage device having stored thereon computer executable instructions for performing a method of representing a virtual dental patient, the method comprising,
receiving a set of clinical records of a patient;
receiving at least one jaw movement record;
determining a control point in a set of target points in the jaw movement record, the control point and the target points comprising points in a lower jaw data set;
determining a location for the set of target points on a first jaw record representing a first position;
aligning a second jaw record representing a second position;
calculating a second location for the target points on the second jaw record; and
determining the at least one helical axis from the first location and the second location, the helical axis comprising at least one parameter determined as a function of the control point.

25. The computer-readable storage device of claim 24, wherein the jaw movement record comprises an excursive record.

* * * * *

UNITED STATES PATENT AND TRADEMARK OFFICE
CERTIFICATE OF CORRECTION

| | | |
|---|---|---|
| PATENT NO. | : 8,013,853 B1 | Page 1 of 2 |
| APPLICATION NO. | : 10/385169 | |
| DATED | : September 6, 2011 | |
| INVENTOR(S) | : Douglas et al. | |

It is certified that error appears in the above-identified patent and that said Letters Patent is hereby corrected as shown below:

On the cover page, item (75), in "Inventors", in column 1, line 1, delete "Falson Heights" and insert -- Falcon Heights --, therefor.

On the cover page, item (56), under "Other Publications", in column 2, line 4, delete "sterotactic" and insert -- stereotactic --, therefor.

On the cover page, item (56), under "Other Publications", in column 2, line 6, delete "adn" and insert -- and --, therefor.

On page 2, under "Other Publications", in column 2, line 2, delete "Dentisrty"," and insert -- Dentistry", --, therefor.

On page 2, under "Other Publications", in column 2, line 5, delete "Orthondontics"," and insert -- Orthodontics", --, therefor.

In the drawings:

On Sheet 18 of 29, Box No. 11, Figure 18, line 1, delete "Creat" and insert -- Create --, therefor.

On Sheet 19 of 29, Box No. 11, Figure 19, line 1, delete "Creat" and insert -- Create --, therefor.

On Sheet 21 of 29, Box No. 11, Figure 21, line 1, delete "Creat" and insert -- Create --, therefor.

On Sheet 28 of 29, Box No. 406, Figure 28, line 3, delete "Positon" and insert -- Position --, therefor.

In column 9, line 40, delete "octtree" and insert -- octree --, therefor.

In column 17, line 6, delete "Fore" and insert -- For --, therefor.

Signed and Sealed this
Eleventh Day of September, 2012

David J. Kappos
*Director of the United States Patent and Trademark Office*

CERTIFICATE OF CORRECTION (continued)
U.S. Pat. No. 8,013,853 B1

In column 20, line 41, in Claim 7, delete "records." and insert -- records, wherein the first and second records are for a patient and wherein the first record includes data from a first point in time and the second record includes data from a second point in time. --, therefor.

In column 20, line 48, in Claim 9, delete "record: and" and insert -- record; and --, therefor.

In column 21, line 11, in Claim 11, delete "record;" and insert -- record; and --, therefor.

In column 22, line 43, in Claim 23, delete "records." and insert -- records, wherein the first and second records are for a patient and wherein the first record includes data from a first point in time and the second record includes data from a second point in time. --, therefor.

In column 22, line 46, in Claim 24, delete "comprising," and insert -- comprising: --, therefor.